(12) United States Patent
McHugh et al.

(10) Patent No.: US 10,624,753 B2
(45) Date of Patent: Apr. 21, 2020

(54) LOCKING SYSTEM

(71) Applicant: Joint Development, LLC, Salt Lake City, UT (US)

(72) Inventors: Dermott J. McHugh, Seattle, WA (US); Chris A. Weaber, Sandy, UT (US); Eric M. Dacus, Salt Lake City, UT (US); James T. Grutta, Draper, UT (US)

(73) Assignee: Joint Development, LLC, Salt Lake City, UT (US)

( * ) Notice: Subject to any disclaimer, the term of this patent is extended or adjusted under 35 U.S.C. 154(b) by 215 days.

(21) Appl. No.: 15/674,356

(22) Filed: Aug. 10, 2017

(65) Prior Publication Data

US 2018/0042729 A1    Feb. 15, 2018

Related U.S. Application Data

(60) Provisional application No. 62/373,529, filed on Aug. 11, 2016.

(51) Int. Cl.
*A61F 2/38* (2006.01)
*F16B 5/02* (2006.01)
*A61F 2/30* (2006.01)

(52) U.S. Cl.
CPC ............ *A61F 2/389* (2013.01); *F16B 5/0233* (2013.01); *A61F 2002/3051* (2013.01); *A61F 2002/30405* (2013.01); *A61F 2002/30411* (2013.01); *A61F 2002/30433* (2013.01); *A61F 2002/30495* (2013.01); *A61F 2002/30512* (2013.01); *A61F 2002/30514* (2013.01); *A61F 2002/30878* (2013.01); *A61F 2002/30884* (2013.01)

(58) Field of Classification Search
CPC ............ A61F 2/389; A61F 2002/30411; F16B 5/0233
See application file for complete search history.

(56) References Cited

U.S. PATENT DOCUMENTS 5,782,920 A * 7/1998 Colleran ................. A61F 2/389
                                                        403/306
8,721,729 B1 * 5/2014 Lu ........................... A61F 2/389
                                                        623/20.15

(Continued)

*Primary Examiner* — Megan Y Wolf
(74) *Attorney, Agent, or Firm* — Lowry Blixseth APC; Scott M. Lowry

(57) ABSTRACT

The orthopedic implant locking system may include an eccentric tibial stem having an engagement rod selectively threadingly engageable with a tibial baseplate, a lock housing securable in rotatable and substantial vertical constrained relation relative to the tibial stem, and an extension lock selectively threadingly engageable with the lock housing and including an inner passage keyed to selectively slidably engage the engagement rod in flush engagement therewith. The extension lock may extend or contract in response to rotational movement of the lock housing simultaneously while the extension lock remains in substantial non-rotatable relation relative to the tibial stem. Engagement of the extension lock with the tibial baseplate may generally vertically and rotationally selectively lock the tibial baseplate with the tibial stem and, based on the threaded spaced relation of the tibial baseplate relative to the tibial stem, linearly and eccentrically axially misalign the tibial stem relative to the tibial baseplate.

31 Claims, 19 Drawing Sheets

(56) References Cited

U.S. PATENT DOCUMENTS

| | | | |
|---|---|---|---|
| 2007/0179628 A1* | 8/2007 | Rochetin | A61F 2/389 623/20.34 |
| 2009/0149963 A1* | 6/2009 | Sekel | A61F 2/30721 623/20.15 |
| 2017/0348105 A1* | 12/2017 | Sun | A61F 2/30734 |

* cited by examiner

LOCKING SYSTEM

BACKGROUND OF THE INVENTION

The present invention generally relates to a locking system. More specifically, the present invention relates to a locking system for positioning one component in linear spaced relation relative to another component by way of conventional rotational threading, wherein when used with orthopedic implants, such spaced relation may linearly and/ or eccentrically position one implant component (e.g., a tibial stem) relative to another implant component (e.g., a tibial baseplate).

Locking systems for positioning one implant component in spaced relation relative to another implant component are generally known in the art, and may be used to adjust the vertical and/or angular positioning of an implantable tibial stem or the like relative to an implantable tibial baseplate or the like. But, such systems known in the art use non-conventional rotational threading. For example, FIGS. 1-6 illustrate a tibial implant 30 having a prior art locking system 32 designed to couple a tibial stem extension 34 relative to a corresponding tibial baseplate 36. More specifically, the prior art locking system 32 includes an angled extension 38 that threadingly engages the tibial stem extension 34 on one end (threads not shown) and threadingly engages the tibial baseplate 36 on the other end by way of a threaded section 39. The threaded section 39 may include a first set of exterior threads 40 (FIGS. 2, 4, and 5) that threadingly engage a series of interior threads within the tibial baseplate 36 and a second set of oppositely threaded exterior threads 41 (FIGS. 2, 5, and 6) that threadingly engage a set of internal threads (not shown) of a locknut 42.

In operation, each of the tibial stem extension 34, the angled extension 38, the locknut 42, and the tibial baseplate 36 are screwed together into the configuration shown in FIG. 3. In this example, rotating the tibial stem extension 34 along the rotational arrow A in FIG. 3 tightens threaded engagement of the tibial stem extension 34 with the angled extension 38, and opposite rotation loosens the threaded engagement therewith. The same is true for threaded engagement of the angled extension 38 with the tibial baseplate 36, i.e., rotating the angled extension 38 along the rotational arrow B in FIG. 3 causes the angled extension 38 to threadingly engage the tibial baseplate 36 along the first set of exterior threads 40, while opposite rotation loosens or disengages the angled extension 38 with respect to the tibial baseplate 36 along the first set of exterior threads 40. The locknut 42 is threaded for engagement with the second set of exterior threads 41, which are oppositely threaded the first set of exterior threads 40. More specifically, in this embodiment, the rotational movement of the locknut 42 along rotational arrow C causes threaded engagement with the angled extension 38 (i.e., the locknut 42 moves along the threads away from the tibial baseplate 36 and toward the angled extension 38 in FIG. 3), while opposite rotation causes the locknut 42 to disengage the angled extension 38 (i.e., the locknut 42 moves along the threads toward the tibial baseplate 36 and away from the angled extension 38 in FIG. 3). When the angled extension 38 and the locknut 42 are rotated commonly along the direction of the rotational arrows B and C, both move in opposite directions. That is, the angled extension 38 threadingly engages the tibial baseplate 36 and the locknut 42 threadingly engages the angled extension 38 and moves away from the tibial baseplate 36. The drawback of this structure is that common rotational movement of the angled extension 38 and the locknut 42 in the direction of rotational of arrows B and C brings the two components together. This inhibits desired locking engagement between the locknut 42 and the tibial baseplate 36. As such, it can be difficult to properly tighten the prior art locking system 32. In this respect, the opposite rotational operation of the locknut 42 is counterintuitive and can be confusing and particularly frustrating during surgery.

To extend the distance between the tibial stem extension 34 and the tibial baseplate 36, the angled extension 38 is unscrewed from the tibial baseplate 36 by some desired distance 44, e.g., as shown in FIG. 4, by way of rotating the angled extension 38 along the rotational arrow B' (FIG. 4) relative to the tibial baseplate 36. The desired distance 44 may be the result of the desired vertical displacement of the tibial stem extension 34 relative to the tibial baseplate 36, or the desired angular positioning of the tibial stem extension 34 by way of being coupled to the angled extension 38. In the position shown in FIG. 4, the first set of exterior threads 40 are re-exposed as a result of backing off (unscrewing) the angled extension 38 from the tibial baseplate 36. Once the desired distance 44 is attained, the tibial stem extension 34 must be locked in place relative to the tibial baseplate 36. This is accomplished by rotating the locknut 42 along rotational arrow C' (FIG. 5) along the exterior threads 40, which causes the locknut 42 to move away from the body of the angled extension 38 and toward the tibial baseplate 36. This is counter-intuitive to conventional threading. In this respect, the locknut 42 is basically tightened up against the tibial baseplate 36 while the tibial stem extension 34 is held in place—FIG. 6 illustrates the locknut 42 engaged up underneath the tibial baseplate 36 in this respect. Hand-tightening the locknut 42 up underneath the tibial baseplate 36 typically does not provide the desired tightening to prevent the locknut 42 from coming loose. Rather, once the locknut 42 is in the position shown in FIG. 6, further tightening is needed by way of rotation of the angled extension 38. This is accomplished by engaging the angled extension 38 with a first wrench or the like and engaging the locknut 42 with a second wrench or the like, then attempting to rotate each in opposite directions, i.e., generally rotating the angled extension 38 along directional arrow B (FIG. 3) to further engage the angled extension 38 with the tibial baseplate 36 and rotating the locknut 42 along rotational arrow C' (FIG. 5) so the locknut 42 is forced to move away from the body of the angled extension 38 and into engagement with the tibial baseplate 36. Although, one problem with this prior art locking system 32 is that opposite rotation along rotational arrows B and C' is counter-intuitive for the locknut 42, namely because it must be rotated opposite to convention to tighten.

There exists, therefore, a significant need in the art for a locking system that permits hand tightening of the locking system in the same or conventional rotational direction commonly associated with tightening a screw or nut to position one component in linear spaced relation relative to another component. The present invention fulfills these needs and provides further related advantages.

SUMMARY OF THE INVENTION

In one embodiment as disclosed herein, an orthopedic implant locking system may include an eccentric tibial stem having an engagement rod selectively threadingly engageable with a tibial baseplate, a lock housing securable in rotatable and substantial vertical constrained relation relative to the tibial stem via the engagement rod, and an extension lock selectively threadingly engageable with the lock housing and including an inner passage keyed to selectively slidably engage the engagement rod in flush engagement therewith. In this embodiment, the extension lock may be extendable relative to the lock housing in response to movement of the lock housing in a first rotational direction simultaneously while the extension lock is in substantial non-rotatable relation relative to the tibial stem. Moreover, the extension lock may also be retractable relative to the lock housing in response to movement of the lock housing in a second rotational direction, opposite the first rotational direction, simultaneously while the extension lock is in substantial non-rotatable relation relative to the tibial stem. Here, engagement of the extension lock with the tibial baseplate generally vertically and rotationally selectively locks the tibial baseplate with the tibial stem and, based on the threaded spaced relation of the tibial baseplate relative to the tibial stem, linearly and eccentrically axially misaligns a first lower elongated section of the tibial stem relative to the tibial baseplate.

The engagement rod may include a keyway configured to selectively receive and retain the inner passage of the extension lock in non-rotatable relation relative thereto. The lock housing may also include an inner channel having a size and shape for selectively receiving and retaining a washer freely rotatable therein. More specifically, the keyway may include at least a pair of planar surfaces cutout from the engagement rod and the washer may include an inner diameter sized for select engagement and retainment within an outwardly presented and generally circumferential collar in the engagement rod for free rotation therein. The engagement rod may further include a first rotational lock section that includes the keyway, a threaded section facilitating threaded engagement with the tibial baseplate, and a relatively smooth cylindrical section intermediate the first rotational lock section and the threaded section. The washer may position the lock housing in a rotatable yet vertically constrained configuration relative to the tibial stem when the washer is simultaneously retained within the inner channel and the collar.

In another aspect of this embodiment, the washer may be formed as a general ring shape having a cut-out permitting opposite edges of the general ring-shaped washer to bend relative to one another. Moreover, the tibial stem may include an adapter having a prefabricated eccentricity and the extension lock may include a generally planar locking head that selectively engages a generally planar landing surface of the tibial baseplate for friction fit engagement therewith to lock the tibial baseplate in vertical and non-rotatable relation relative to the tibial stem. When the first rotational direction is clockwise and the second rotational direction is counter-clockwise, opposite rotation of the tibial baseplate relative to the lock housing may cause engagement between the locking head and the landing surface. Common rotational movement of the tibial stem and the lock housing, and opposite the tibial baseplate, may cause engagement between the locking head and the landing surface.

In another embodiment as disclosed herein, the locking system may include a first component selectively threadingly engageable with a second component, a lock housing securable in rotatable and substantial vertical constrained relation relative to the first component, and an extension lock selectively threadingly engageable with the lock housing and extendable relative to the lock housing in response to movement of the lock housing in a first rotational direction simultaneously while the extension lock is in substantial non-rotatable relation relative to the first component and retractable relative to the lock housing in response to movement of the lock housing in a second rotational direction opposite the first rotational direction simultaneously while the extension lock is in substantial non-rotatable relation relative to the first component. Here, engagement of the extension lock with the second component may generally vertically and rotationally selectively lock the second component with the first component. When fully assembled, the lock housing may be in rotatable relation relative to the engagement rod and the extension lock may be in non-rotatable relation relative to the engagement rod.

In this embodiment, the first component may include a keyway configured to selectively receive and retain the extension lock in non-rotatable relation relative thereto. The keyway may more specifically include at least a pair of planar surfaces cutout from an otherwise generally cylindrical engagement rod extending out from one side of the first component. The extension lock may include an inner passage keyed to match the at least pair of planar surfaces for substantial flush engagement therewith when selectively slidably engaged with the engagement rod. The engagement rod itself may include a first rotational lock section including the keyway, a threaded section facilitating threaded engagement with the second component, and a relatively smooth cylindrical section intermediate the first rotational lock section and the threaded section.

In another aspect of this embodiment, the lock housing may include an inner channel having a size and shape for selectively receiving and retaining a washer freely rotatable therein. The washer may include an inner diameter sized for select engagement and retainment within an outwardly presented and generally circumferential collar in the first component for free rotation therein. The washer may thus position the lock housing in a rotatable yet vertically constrained configuration relative to the first component when the washer is simultaneously retained within the inner channel and the collar. As such, the washer may be made of a general ring shape having a cut-out permitting opposite edges of the general ring-shaped washer to bend relative to one another to snap into the inner channel and/or the collar.

Moreover, the first component may include a first lower elongated section and a second upper eccentric section generally axially misaligned from the lower elongated section. In this embodiment, the first component may include an eccentric tibial stem and the second component may include a tibial baseplate. The threaded spaced relation of the tibial baseplate relative to the tibial stem may linearly and eccentrically axially misalign a first lower elongated section of the tibial stem relative to the tibial baseplate. Additionally, the first component may be an adapter having a prefabricated eccentricity that facilitates said axial misalignment.

In another aspect of these embodiments, the extension lock may include a generally planar locking head that selectively engages a generally planar landing surface of the second component for friction fit engagement therewith to lock the second component in vertical and non-rotatable relation relative to the first component. Here, when the first rotational direction is clockwise and the second rotational direction is counter-clockwise, opposite rotation of the second component relative to the lock housing may cause engagement between the locking head and the landing surface. Similarly, common rotational movement of the first component and the lock housing, and opposite that of the second component, may cause engagement between the locking head and the landing surface.

In another embodiment, the locking system as disclosed herein may include a first component selectively threadingly engageable with a second component, a lock housing including an inner channel having a size and shape for selectively receiving and retaining a washer freely rotatable therein and securable in rotatable and substantial vertical constrained relation to the first component, and an extension lock selectively threadingly engageable with the lock housing and selectively slidably engageable with the first component via a keyway configured to retain the extension lock in non-rotatable relation relative thereto, wherein the extension lock may be extendable relative to the lock housing in response to movement of the lock housing in a first rotational direction simultaneously while the extension lock is in substantial non-rotatable relation relative to the first component and retractable relative to the lock housing in response to movement of the lock housing in a second rotational direction opposite the first rotational direction simultaneously while the extension lock is in substantial non-rotatable relation relative to the first component. Here, engagement of a generally planar locking head of the extension lock with a generally planar landing surface of the second component may generally vertically and rotationally selectively lock the second component with the first component. Additionally, when the first rotational direction is a clockwise direction and the second rotational direction is a counter-clockwise direction, opposite rotation of the second component relative to the lock housing may cause engagement between the locking head and the landing surface. Additionally, the lock housing may be in rotatable relation relative to the engagement rod simultaneously while the extension lock may be in non-rotatable relation relative to the engagement rod.

More specifically, the keyway may include at least a pair of planar surfaces cutout from an otherwise generally cylindrical engagement rod extending out from one side of the first component. The extension lock may include an inner passage keyed to match the at least pair of planar surfaces for substantial flush engagement therewith when selectively slidably engaged with the engagement rod. The engagement rod itself may include a first rotational lock section including the keyway, a threaded section facilitating threaded engagement with the second component, and a relatively smooth cylindrical section intermediate the first rotational lock section and the threaded section.

The washer may include a general ring shape having a cut-out permitting opposite edges thereof to bend relative to one another and may include an inner diameter sized for select engagement and retainment within an outwardly presented and generally circumferential collar in the first component for free rotation therein. The washer may position the lock housing in a rotatable yet vertically constrained configuration relative to the first component when the washer is simultaneously retained within the inner channel and the collar. Additionally, the first component may include an eccentric tibial stem having a first lower elongated section and a second upper eccentric section generally axially misaligned from the lower elongated section. The second component may include a tibial baseplate, wherein threaded spaced relation of the second component relative to the first component linearly and eccentrically axially misaligns the first lower elongated section relative to the second component. The first component may include an adapter having a prefabricated eccentricity to help axially misalign the tibial stem from the tibial baseplate.

In another embodiment, the locking mechanism disclosed herein may include a tibial stem having an outwardly extending engagement rod that includes a first or lower rotational lock section, a second or mid non-threaded smooth section, and a third or upper threaded section. The engagement rod may be of a size and shape for select slide-on reception and axial constraint of a lock housing having an internal lock washer that resides in an internal channel and snaps into or otherwise engages a substantially circumferential extension or outer collar outwardly protruding from the surface of the lower rotational lock section of the engagement rod. This selectively vertically positions the lock housing along the engagement rod, while simultaneously permitting the lock housing to rotate freely relative to the tibial stem. The lock housing further includes an interior surface threaded for engagement with an extension lock having a first lower threaded end and a second upper locking head configured for friction fit engagement up underneath the tibial baseplate. The extension lock includes an internal geometry keyed to engage the rotational lock section to prevent relative rotational movement of the extension lock relative to the engagement rod. In this respect, rotation of the lock housing in a first rotational direction may cause commensurate extension of the extension lock out from within the lock housing by way of relative rotational movement of the internal/external threads and by virtue that the rotational lock section prevents relative rotational movement of the extension lock, while simultaneously permitting relative rotational movement of the lock housing.

In operation, the tibial stem may initially be fully threadingly engaged with the tibial baseplate, with the lock housing and fully retracted extension lock sandwiched in between. The first step is to disengage the tibial stem from the tibial baseplate through disengaging rotation of the tibial baseplate relative thereto. This causes the tibial baseplate to move away from the tibial stem. That is, the tibial baseplate may be positioned in linear spaced relation relative to the tibial stem by a desired gap distance. Once the gap distance is reached, the locking system can lock the tibial stem in place relative to the tibial baseplate by extension of the extension lock. In this respect, the next step is to rotate the lock housing to extend the extension lock until the locking head engages the landing surface of the tibial baseplate to "lock" thereto. This effectively locks the tibial stem relative to the tibial baseplate in linear spaced relation relative thereto. To further or "finally" tighten the locking mechanism, the tibial stem may be further rotated to cause engagement of the tibial baseplate with the threadingly engaged tibial stem. As such, one can hand tighten the tibial implant in the desired position without the need to oppositely grip (e.g., by way of a wrench) and oppositely rotate several components. Moreover, such rotational characteristics causes engagement of all components, including the tibial stem, the locking head, and the tibial baseplate, as opposed to engagement of some components, while causing relative disengagement of other components, as discussed above in detail with respect to the prior art locking system.

In one embodiment, the tibial stem may include an angled tibial stem having a first or lower elongated vertical section and a second or upper angled section. In this embodiment, a central axis of the angled tibial stem may be generally vertically misaligned from the central axis of the generally lower elongated section. As such, the desired gap distance may be set based on the overall linear spaced relation of the tibial baseplate relative to the angled tibial stem (e.g., a desired vertical height of the overall tibial implant, such as from the tip of the angled tibial stem on one side to the top of the tibial baseplate on the other) or attaining the desired angular offset or eccentricity of the angled tibial stem (i.e., rotation of the tibial stem causes commensurate angular rotation of the lower elongated section axially misaligned with the upper angled section).

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
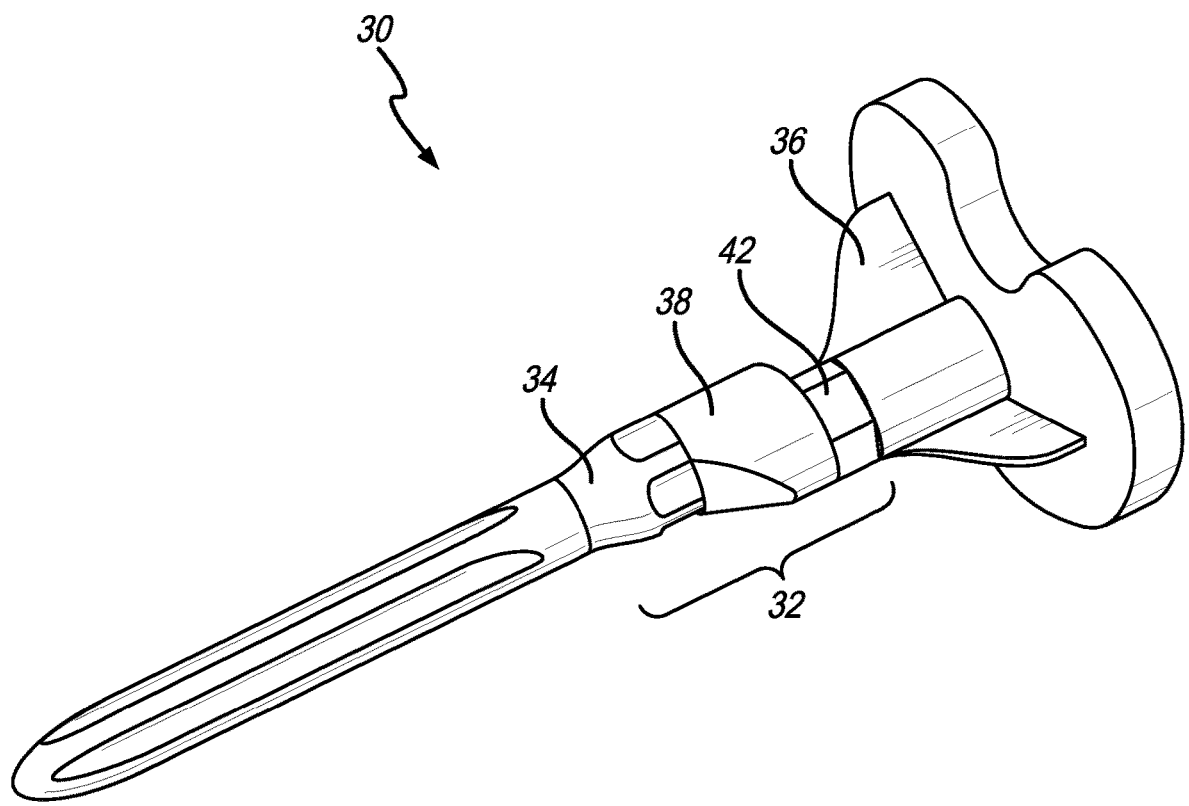
FIG. 1 is a perspective view of a tibial implant including a prior art locking system.
Figure 2:
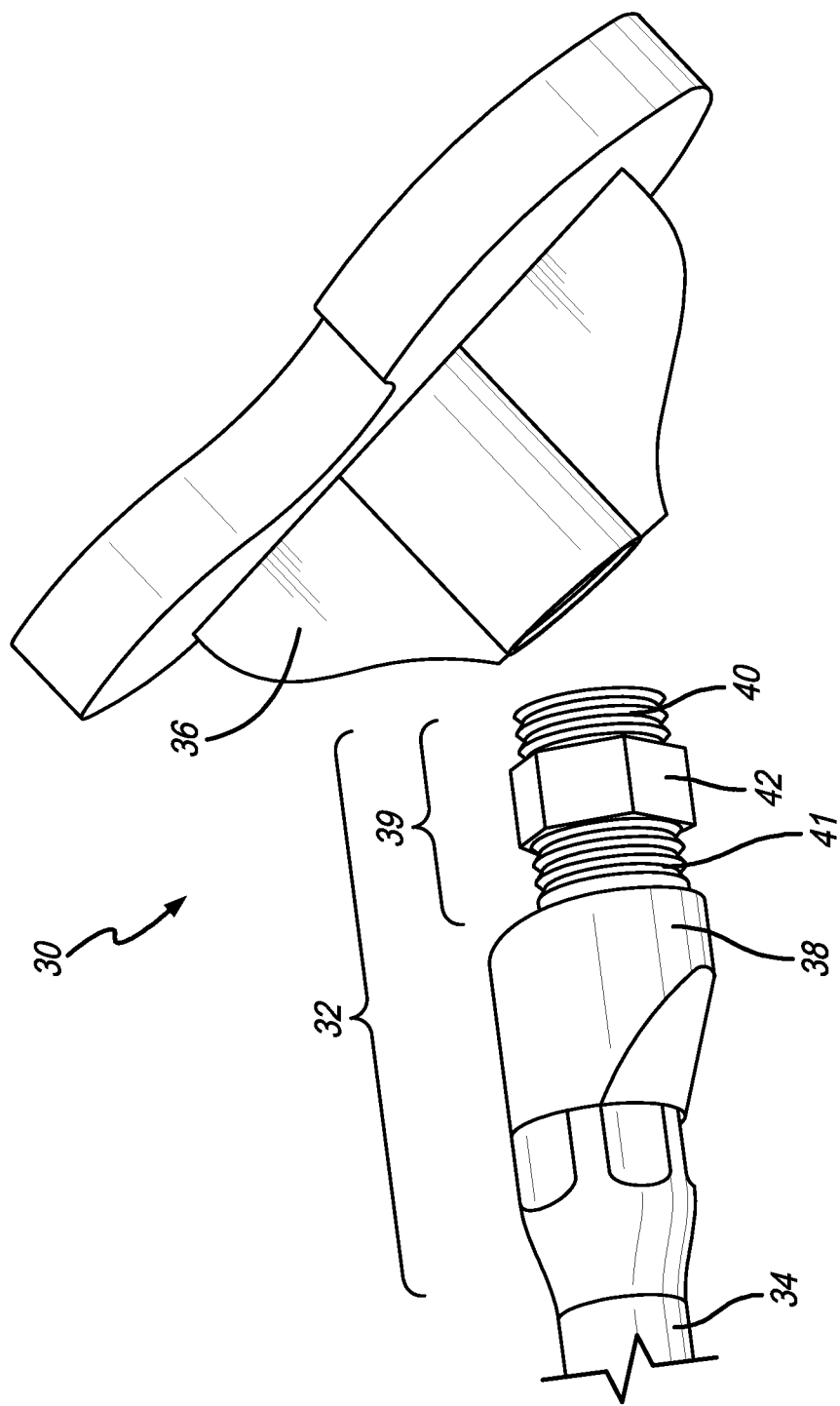
FIG. 2 is a generally exploded perspective view of the prior art locking system of FIG. 1.
Figure 3:
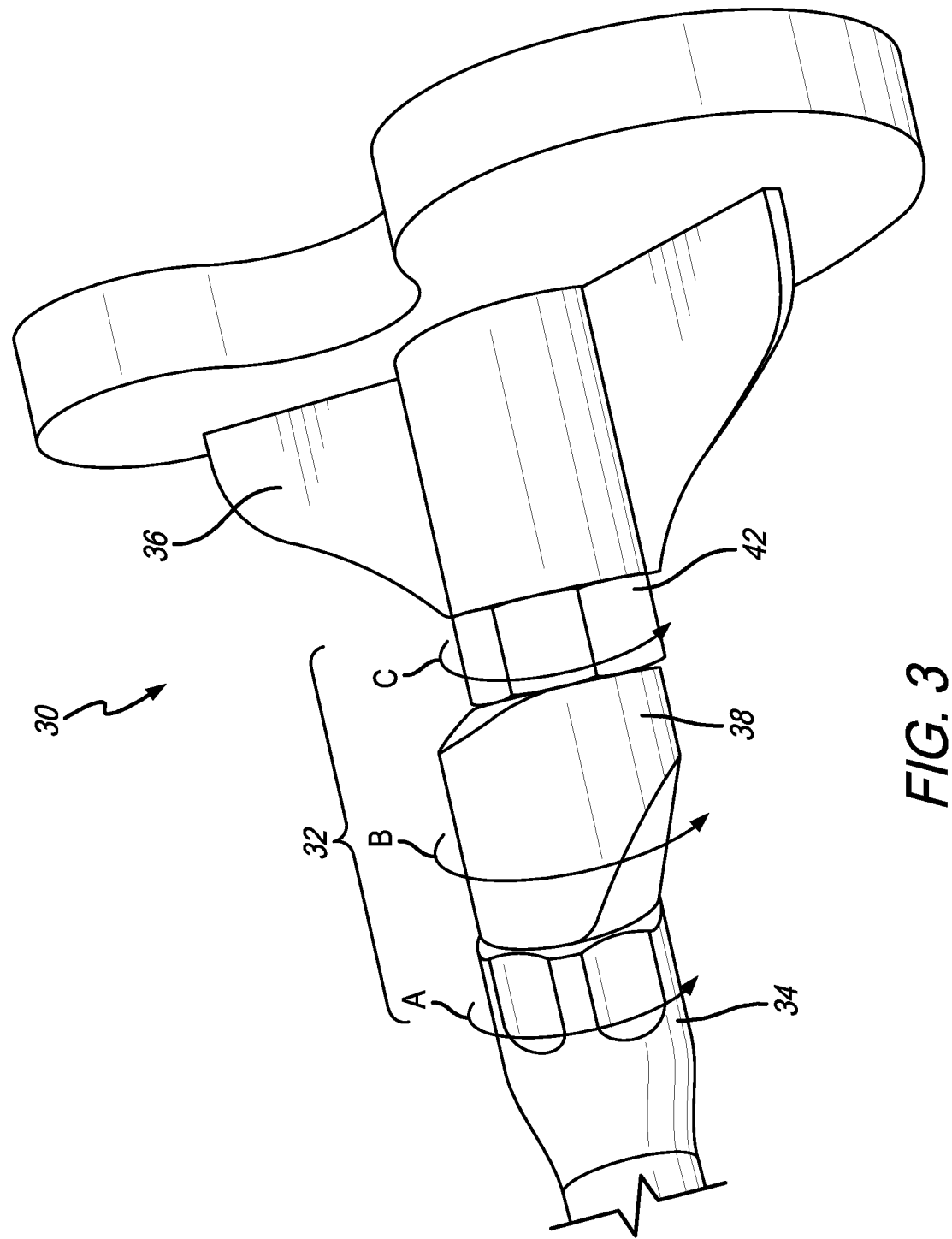
FIG. 3 is an enlarged perspective view of the prior art locking system of FIG. 1, wherein each of a tibial stem extension, an angled extension, a locknut and a tibial baseplate are fully threadingly engaged with one another.
Figure 4:
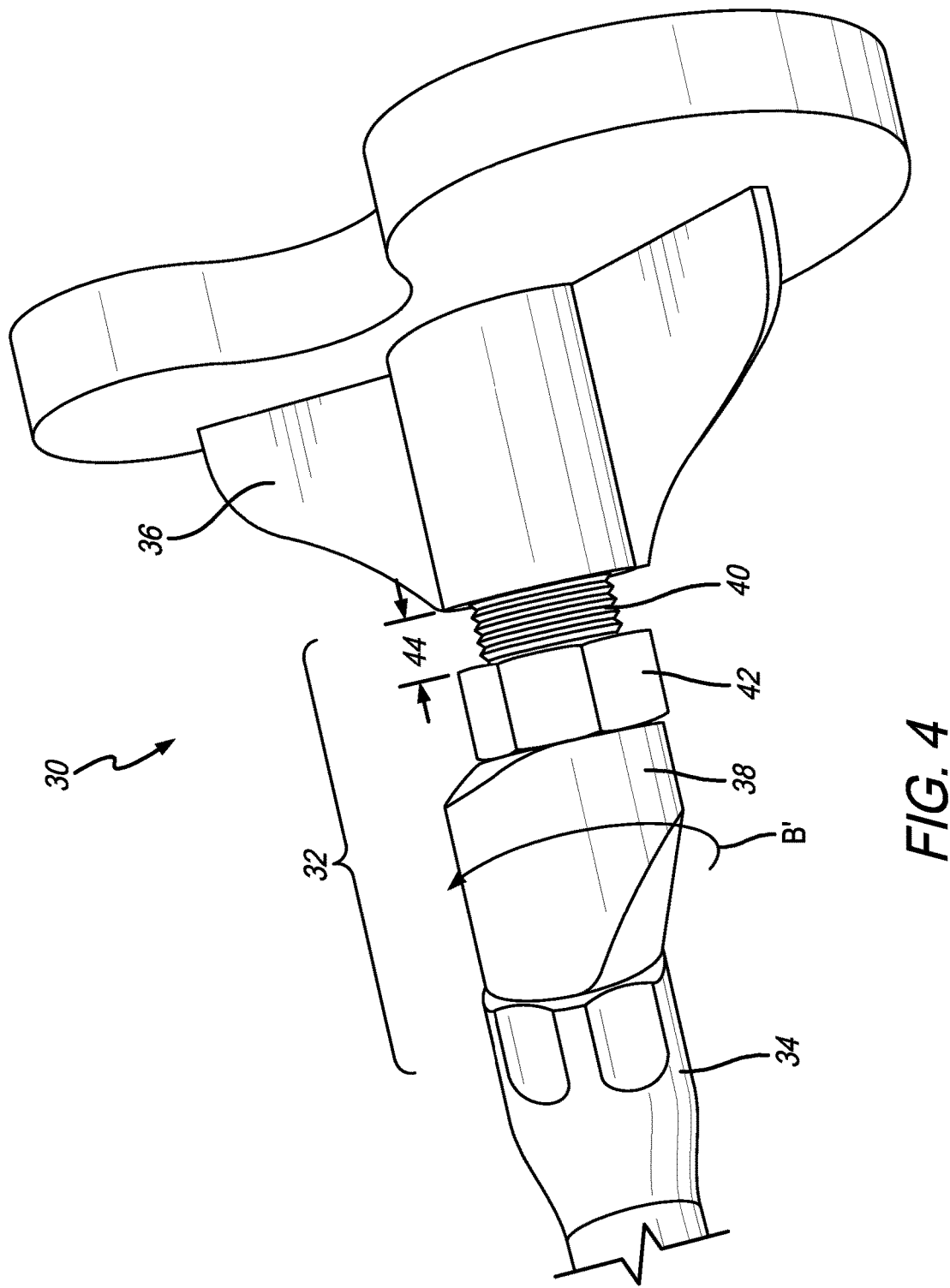
FIG. 4 is an enlarged perspective view similar to FIG. 3, illustrating the angled extension threadingly disengaged from the tibial baseplate by a desired distance.
Figure 5:
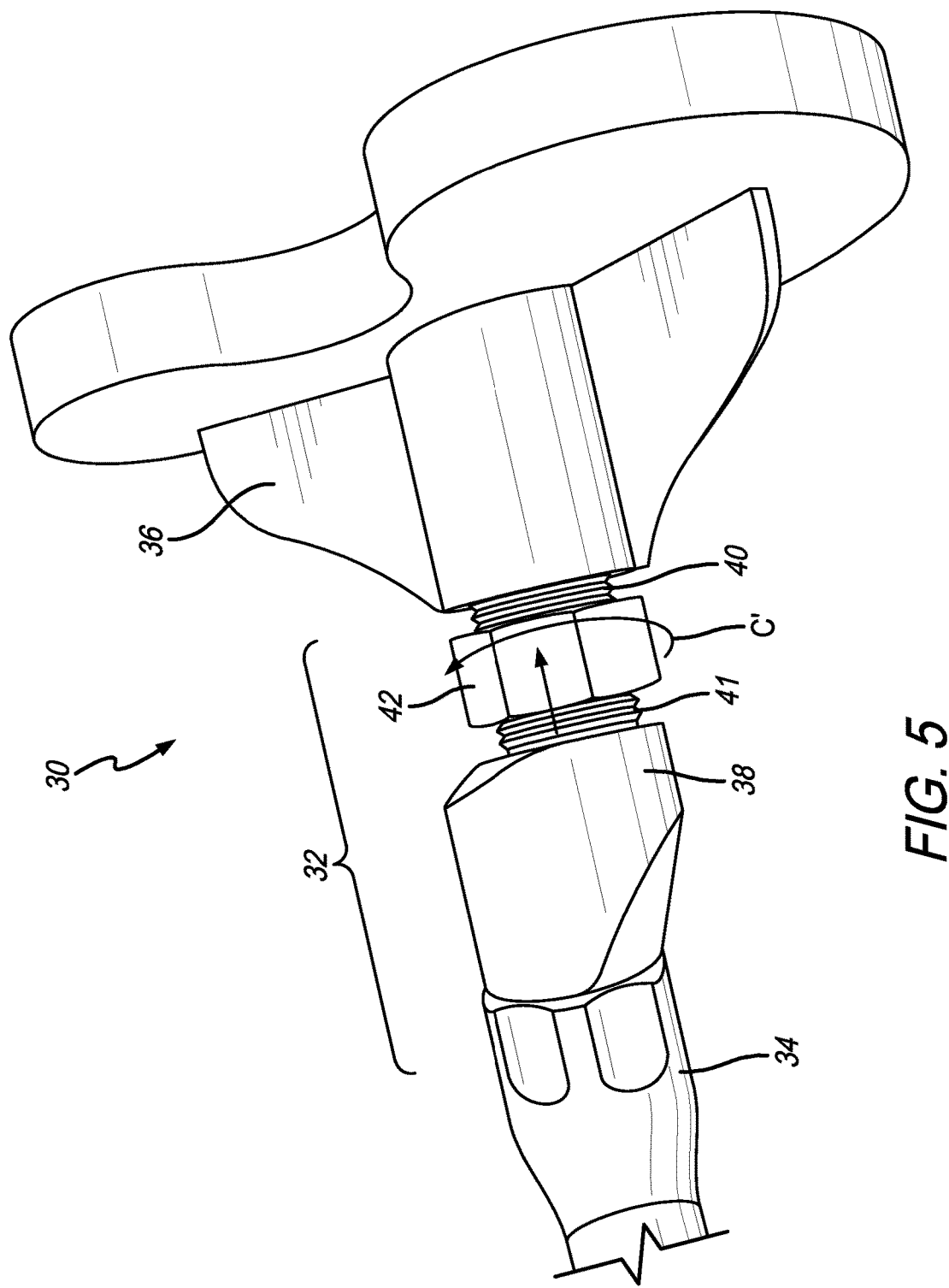
FIG. 5 is an enlarged perspective view similar to FIGS. 3 and 4, illustrating rotational disengagement of the locknut from the angled extension.
Figure 6:
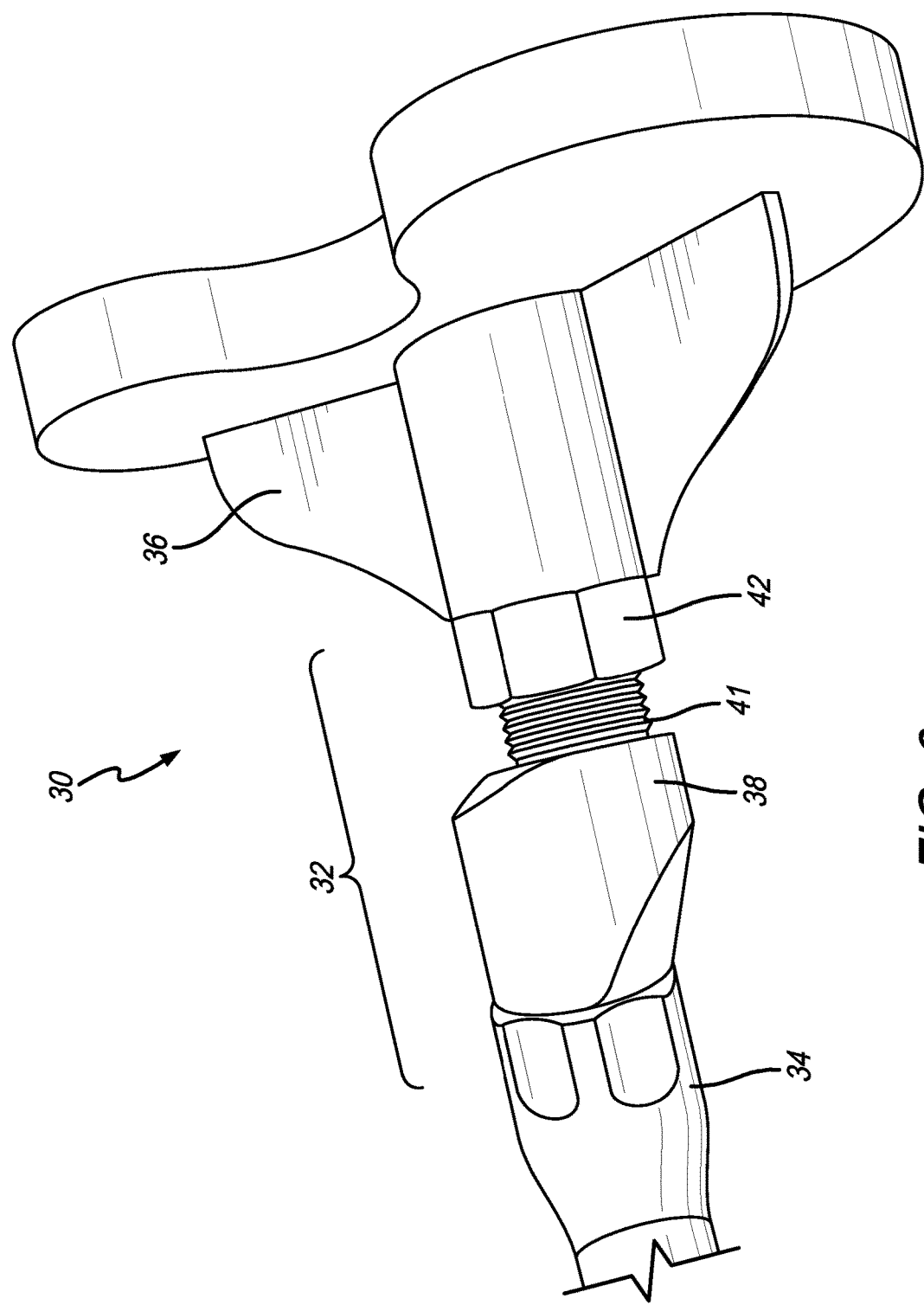
FIG. 6 is an enlarged perspective view similar to FIGS. 3-5, illustrating engagement of the locknut underneath the tibial baseplate.
Figure 7:
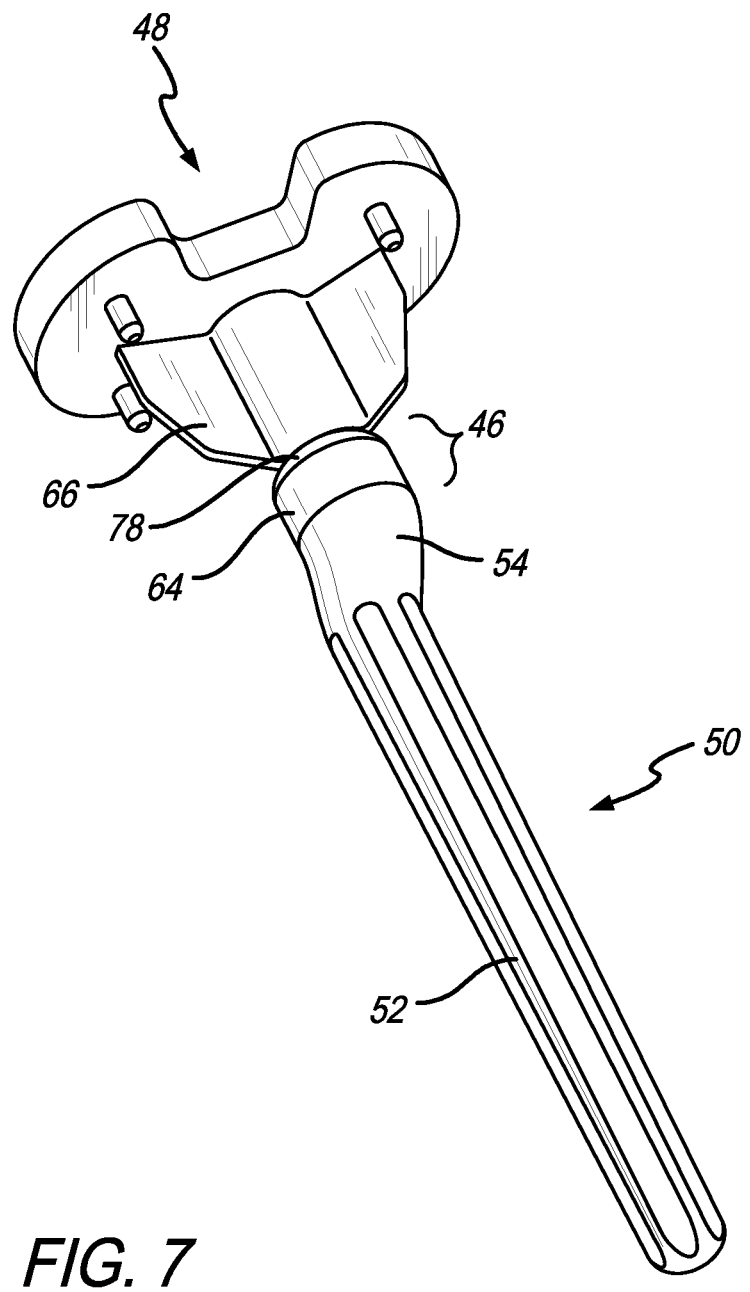
FIG. 7 is a perspective view of a tibial implant incorporating an improved locking system as disclosed herein.
Figure 8:
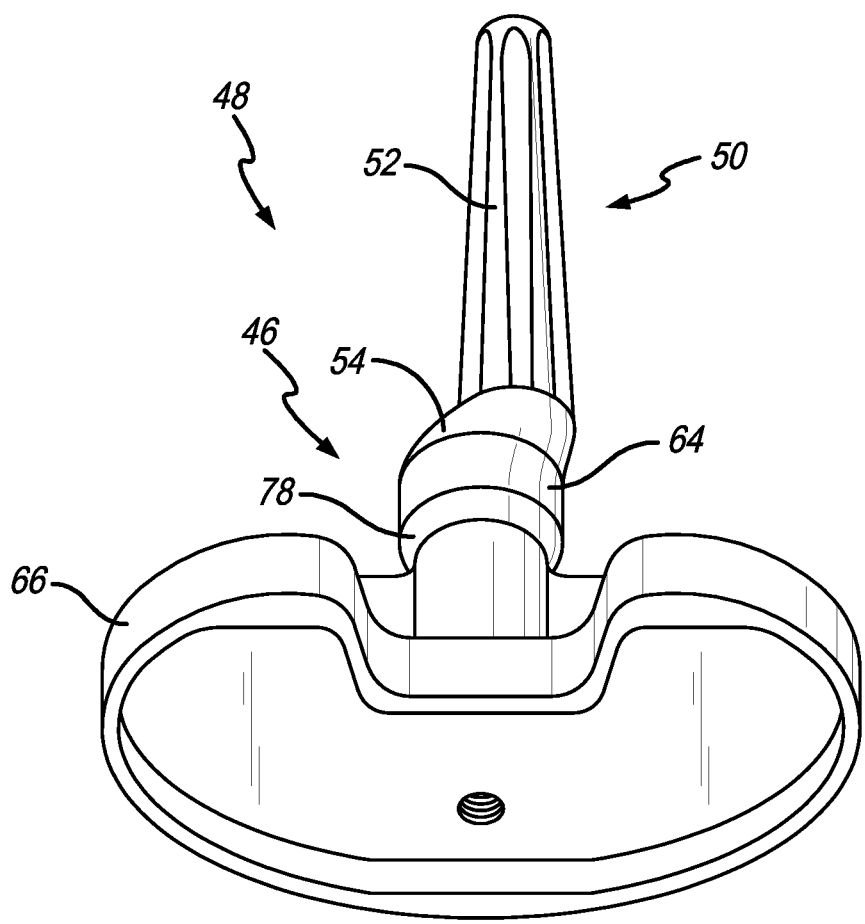
FIG. 8 is a top perspective view of the tibial implant of FIG. 7, more specifically illustrating axial misalignment of a lower elongated section relative to an upper eccentric section of an eccentric tibial stem.
Figure 9:
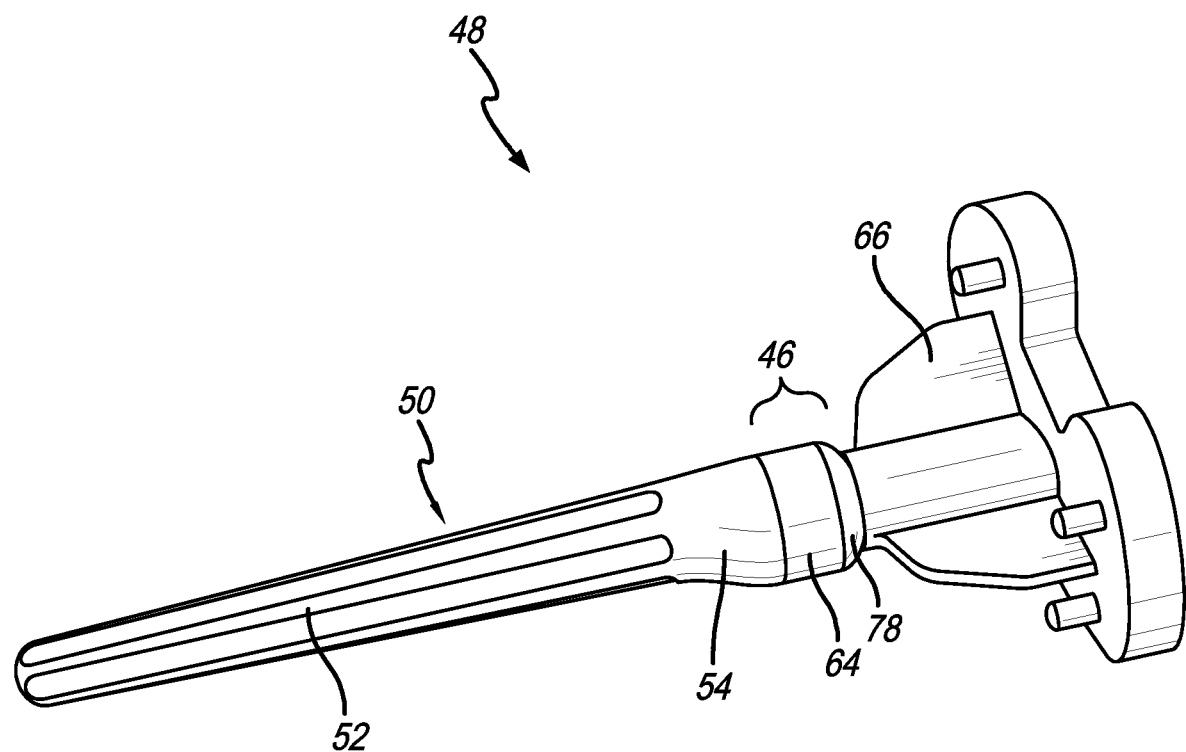
FIG. 9 is another perspective view of the tibial implant of FIGS. 7 and 8.
Figure 10:
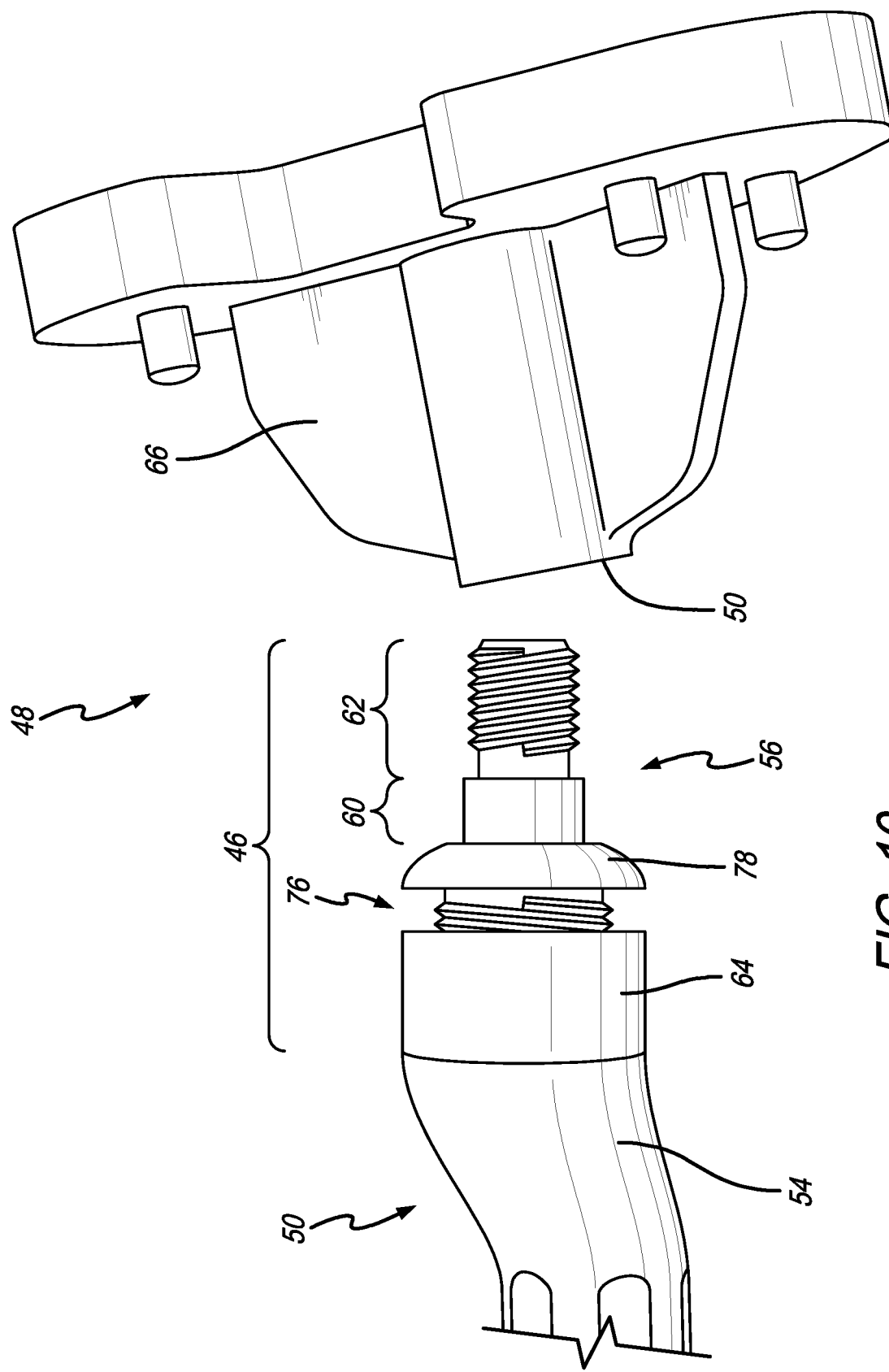
FIG. 10 is a generally exploded perspective view more specifically illustrating the improved locking system of FIGS. 7-9.
Figure 14:
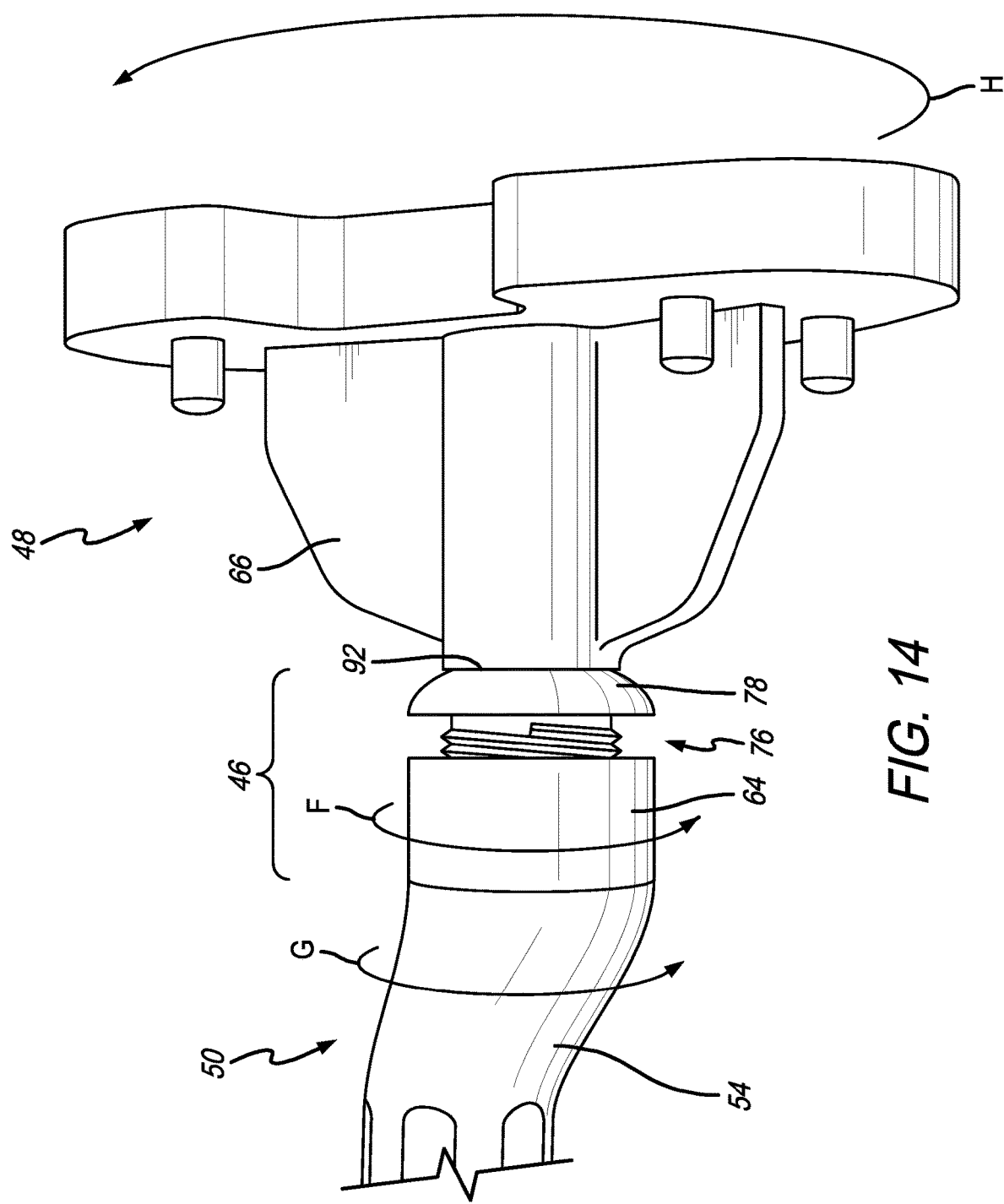
FIG. 14 is an enlarged perspective view similar to FIGS. 11-13, illustrating engagement of the locking head underneath the tibial baseplate.
Figure 15:
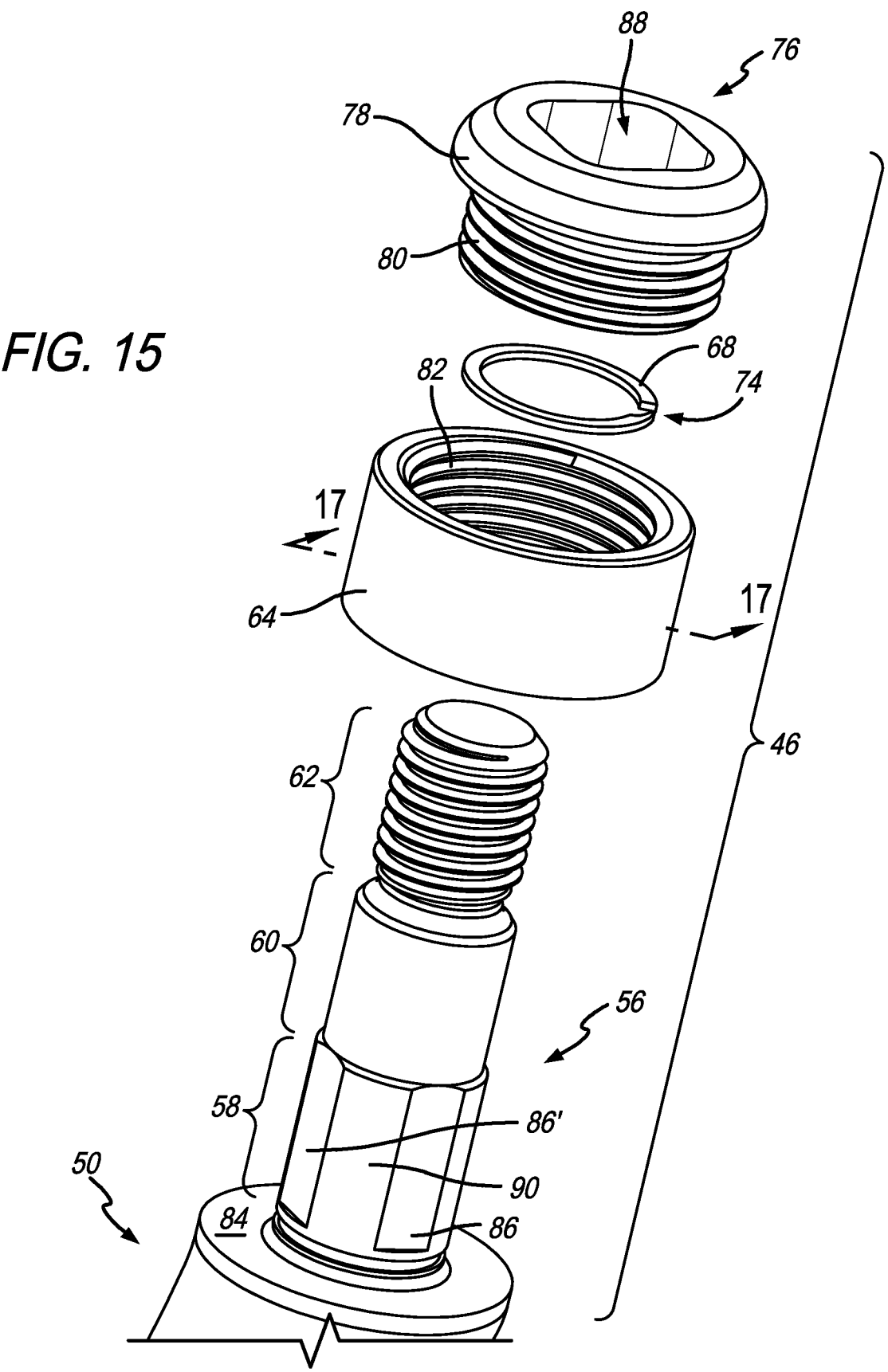
FIG. 15 is an exploded perspective view of the locking system as disclosed herein.
Figure 16:
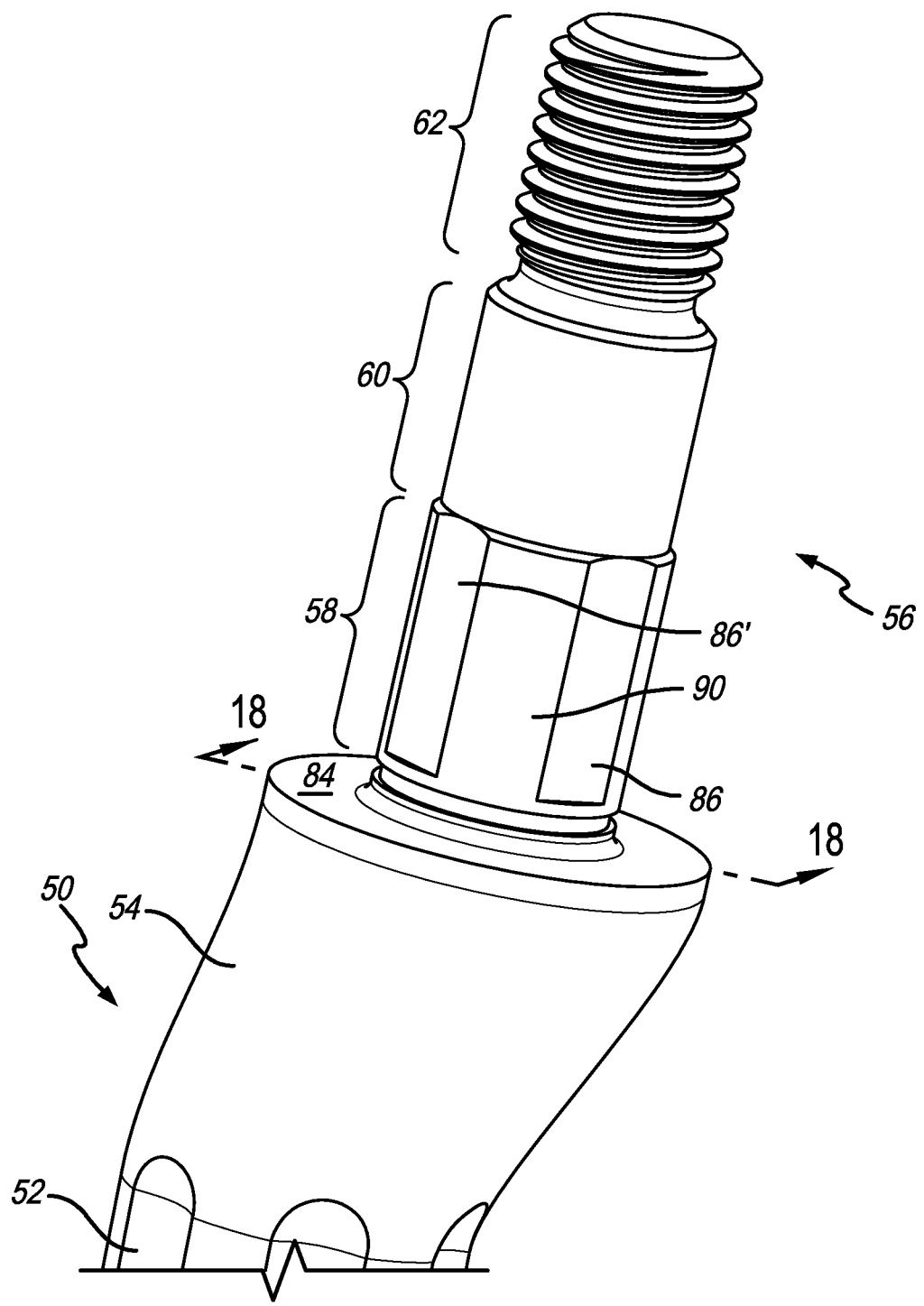
FIG. 16 is a perspective view of an exposed engagement rod, further illustrating a lower rotational lock section, a mid smooth cylindrical section, and an upper threaded section.
Figure 18:
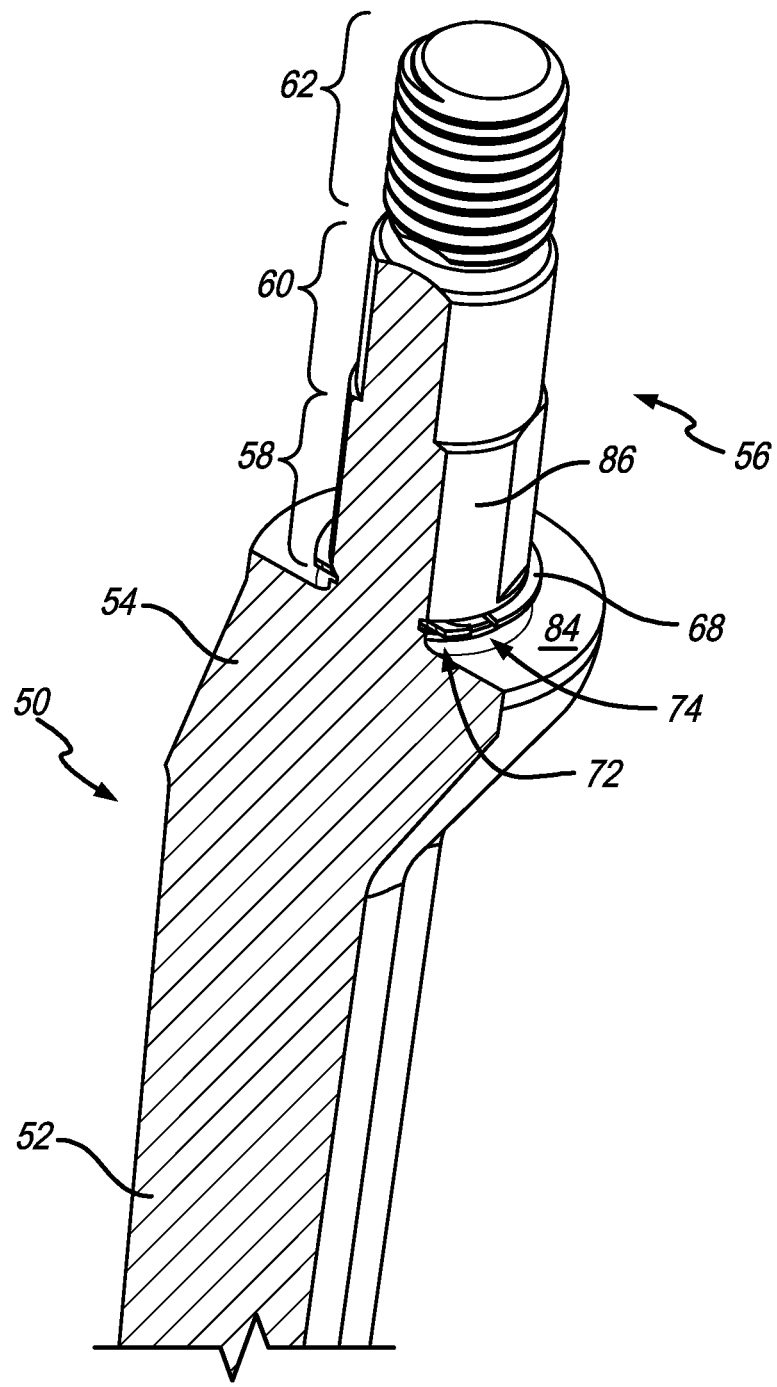
FIG. 18 is a partial cross-sectional view of the eccentric tibial stem and the engagement rod generally taken generally about the line 18-18 in FIG. 16, further illustrating engagement of the internal lock washer with a collar in the lower rotational lock section.
Figure 19:
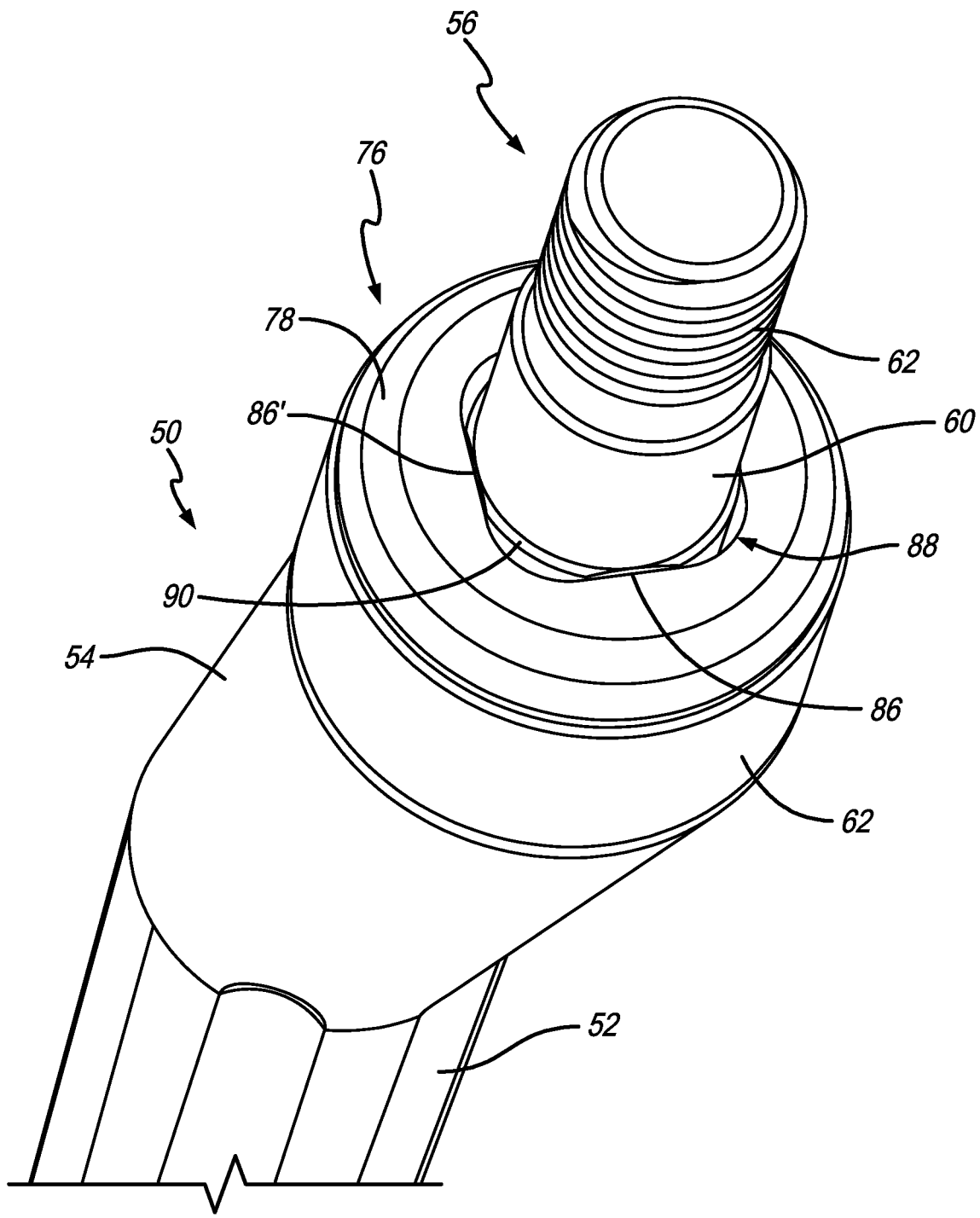
FIG. 19 is a top perspective view of the engagement rod extending up from the eccentric tibial stem, further illustrating the extension lock engaged therewith in non-rotatable relation.

As shown in the exemplary drawings for purposes of illustration, an improved locking system as disclosed herein is referred to generally in FIGS. 7-15 by reference numeral 46. In particular, the locking system 46 is illustrated in FIGS. 7-15 integrated into a tibial implant 48, although a person of ordinary skill in the art will readily recognize that the improved locking system 46 disclosed herein could be adapted or otherwise integrated for use with other tibial implants, such as the tibial implant 30 described above with respect to FIGS. 1-6, or even other implants or devices in general that require one component to be locked in linear spaced relation or at an eccentric position relative to another component. As shown in FIGS. 7-14, the exemplary tibial implant 48 includes an eccentric tibial stem 50 having a first or lower elongated section 52 and a second or upper eccentric section 54 generally axially misaligned from the lower elongated section 52, as best shown in FIGS. 7-9. Extending from the upper angled section 52 is a relatively smaller diameter engagement rod 56 having a first or lower rotational lock section 58, a second or mid level smooth cylindrical section 60, and a third or upper threaded section 62, as best shown in FIGS. 15-16 and 18. The lower rotational lock section 58 is configured for slide-on engagement of a lock housing 64. The lock housing 64 may include an outer diameter approximately equal to the outer diameter or width of the upper eccentric section 54 of the eccentric tibial stem 50 to provide a smooth transition therebetween when located thereon. The upper threaded section 62 is configured for threaded engagement with a tibial baseplate 66, as generally shown in FIGS. 7-9 and 11-14.

Figure 17:
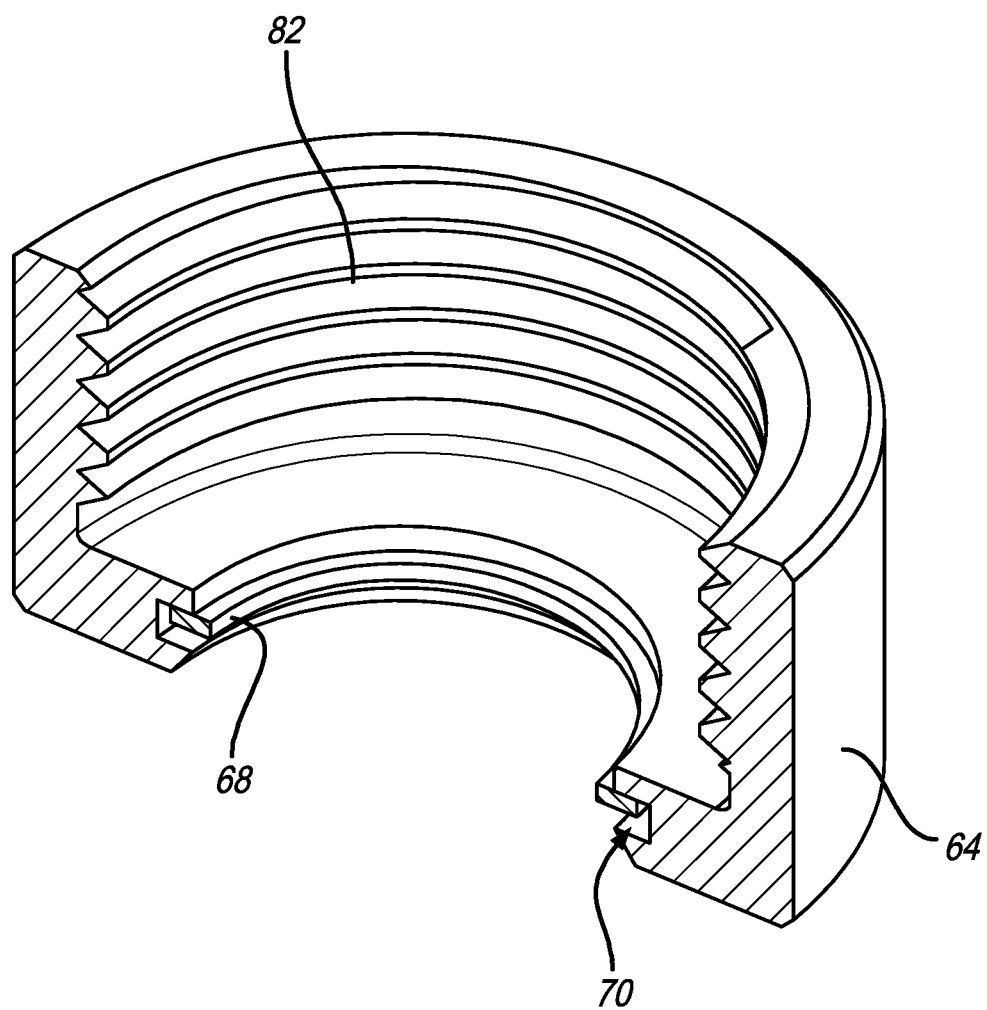
FIG. 17 is a cross-sectional view of the lock housing taken about the line 17-17 in FIG. 15, further illustrating an internal lock washer disposed within a channel in the lock housing.

As shown best in FIGS. 15 and 17, the lock housing 64 includes an internal lock washer 68 that selectively snaps into or otherwise freely rotatably resides in a channel 70 (FIG. 17) therein and engages a substantially circumferential collar 72 (FIG. 18) formed from a portion of the lower rotational lock section 58 near the upper eccentric section 54 of the eccentric tibial stem 50. The internal lock washer 68 is shown having a general ring shape with a cut-out 74 that permits opposite sides of the internal lock washer 68 to displace or bend relative to one another. This permits temporary deformation of the lock washer 68 from a common plane, to facilitate snap-fit engagement with the channel 70 and/or the collar 72. Once engaged, the lock washer 68 may displace back to a static state in a single plane to permit spinning rotation within the channel 70 and/or the collar 72. As such, the internal lock washer 68 maintains the general position of the lock housing 64 in the position shown in FIGS. 7-14, i.e., adjacent the upper eccentric section 54 of the eccentric tibial stem 50, while permitting the lock housing 64 to freely rotate relative to the rotational lock section 58 of the eccentric tibial stem 50 and/or relative to the tibial baseplate 66. This allows for vertical deployment of an extension lock 76 (FIGS. 10, 13-15, and 19) having a locking head 78 (FIGS. 7-15 and 19) that selectively engages the bottom of the tibial baseplate 66, as discussed in detail herein. Although, in an alternative embodiment, the locking system 46 may also be assembled without the use of the internal lock washer 68.

As shown generally in the exploded perspective view of FIG. 15, each of the lock housing 64, the lock washer 68, and the extension lock 76 have a size and shape for select slide-on engagement with the engagement rod 56, and specifically such that the rotational lock section 58, the smooth cylindrical section 60, and the threaded section 62 can extend therethrough. To install, the extension lock 76 may first be engaged with the lock housing 64, such as by way of threaded engagement of a set of external threads 80 on the extension lock 76 with a set of internal threads 82 within the lock housing 64. Once fully engaged (e.g., as shown in FIGS. 9, 11-12, and 19), the lock housing 64 (with the lock washer 68 snapped into the channel 70, as described above) and the threadingly engaged extension lock 76 may slide over the engagement rod 56 for positioning adjacent the upper eccentric section 54 of the eccentric tibial stem 50. Applying a downward force to the locking head 78 may deform or otherwise bend the internally positioned lock washer 68 into engagement with the collar 72 as described above. In this respect, the lock housing 64 is positioned above a top surface 84 of the upper eccentric section 54 to permit clear rotation of the lock housing 64 relative thereto.

FIGS. 15, 16 and 18 illustrate that the lower rotational lock section 58 includes a set of planar sides 86 formed within the otherwise circular geometry of the rotational lock section 58. The extension lock 76 includes an inner passage 88 having a generally rectangular or square geometry that may be keyed to or otherwise positioned flush against the planar sides 86 when the combination of the lock housing 64 and the extension lock 76 are engaged with the engagement rod 56. As a result, the inner passage 88 is sized for slide-on engagement with the rotational lock section 58, but only insofar as the square or rectangular inner passage 88 may have its sides aligned for flush engagement adjacent the planar sides 86. The planar sides 86 are effectively planar recesses within the cylindrical outer-housing of the rotational lock section 58. The planar sides 86 engage the planar faces of the inner passage 88, thereby preventing the extension lock 76 from rotating relative to the engagement rod 56. Moreover, a set of flared or rounded surfaces 90 are located in between the planar sides 86 and engage the inner diameter of the lock housing 64 to axially locate the lock housing 64 relative to the engagement rod 56. Such a keyed configuration between the inner passage 88 of the extension lock 76 and the planar sides 86, 86' of the rotational lock section 58, including the rounded surfaces 90, is shown best in FIG. 19.

At least initially, the eccentric tibial stem 50 is preferably fully threadingly engaged with the tibial baseplate 66 with the extension lock 76 fully seated within the lock housing 64 as shown best in FIGS. 7-9. Here, as best shown in FIG. 8, the central axis of the upper eccentric section 54 of the eccentric tibial stem 50 is misaligned relative to the central axis of the lower elongated section 52 and the centerline or central axis of the symmetrical tibial baseplate 66. The eccentric tibial stem 50 may be of a single piece construction, i.e., the lower elongated section 52 may be integrally formed with the upper eccentric section 54, or the eccentric tibial stem 50 may be formed from two or more components, e.g., the lower elongated section 52 may be configured to selectively engage and/or disengage the upper eccentric section 54. In the latter embodiment, the doctor or surgeon may have the option of mixing and/or matching lower elongated sections 52 that vary in size, shape and construction (e.g., length and/or width) with upper eccentric sections that also vary in size, shape and construction (e.g., length, width, angle, etc.). Such features may provide for more customization during surgery, to fit specific patient needs.

Figure 11:
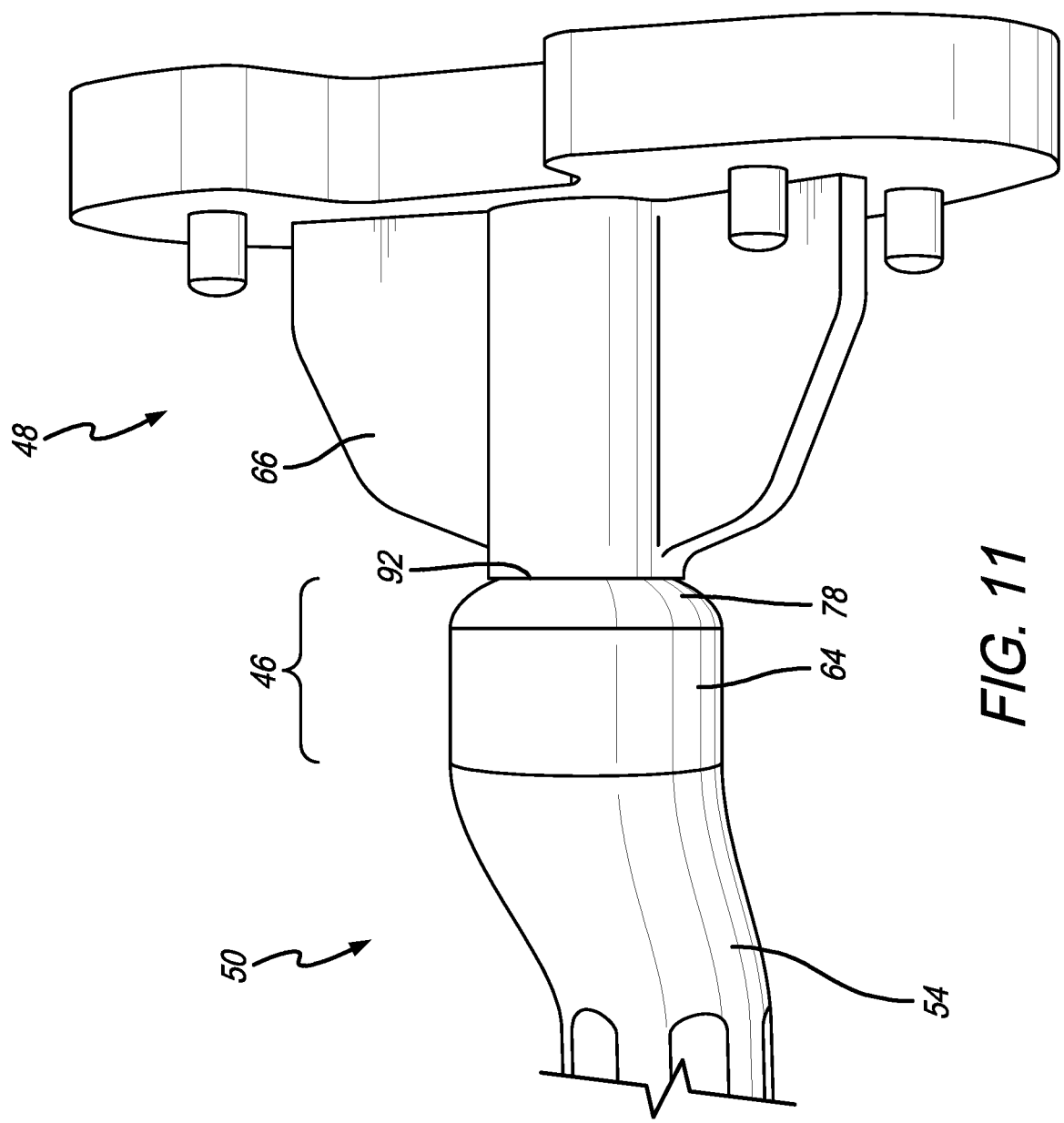
FIG. 11 is an enlarged perspective view of the locking system of FIGS. 7-10, wherein each of an eccentric tibial stem, a lock housing with a locking head threadingly coupled thereto, and a tibial baseplate are fully threadingly engaged with one another.

Also, when in the initial position shown in FIGS. 7-9, the locking head 78 is generally fully seated and flush within the lock housing 64 and flush against or otherwise adjacent to a landing surface 92 (FIG. 11) of the tibial baseplate 66, such as shown specifically in the enlarged perspective view of FIG. 11.

Figure 12:
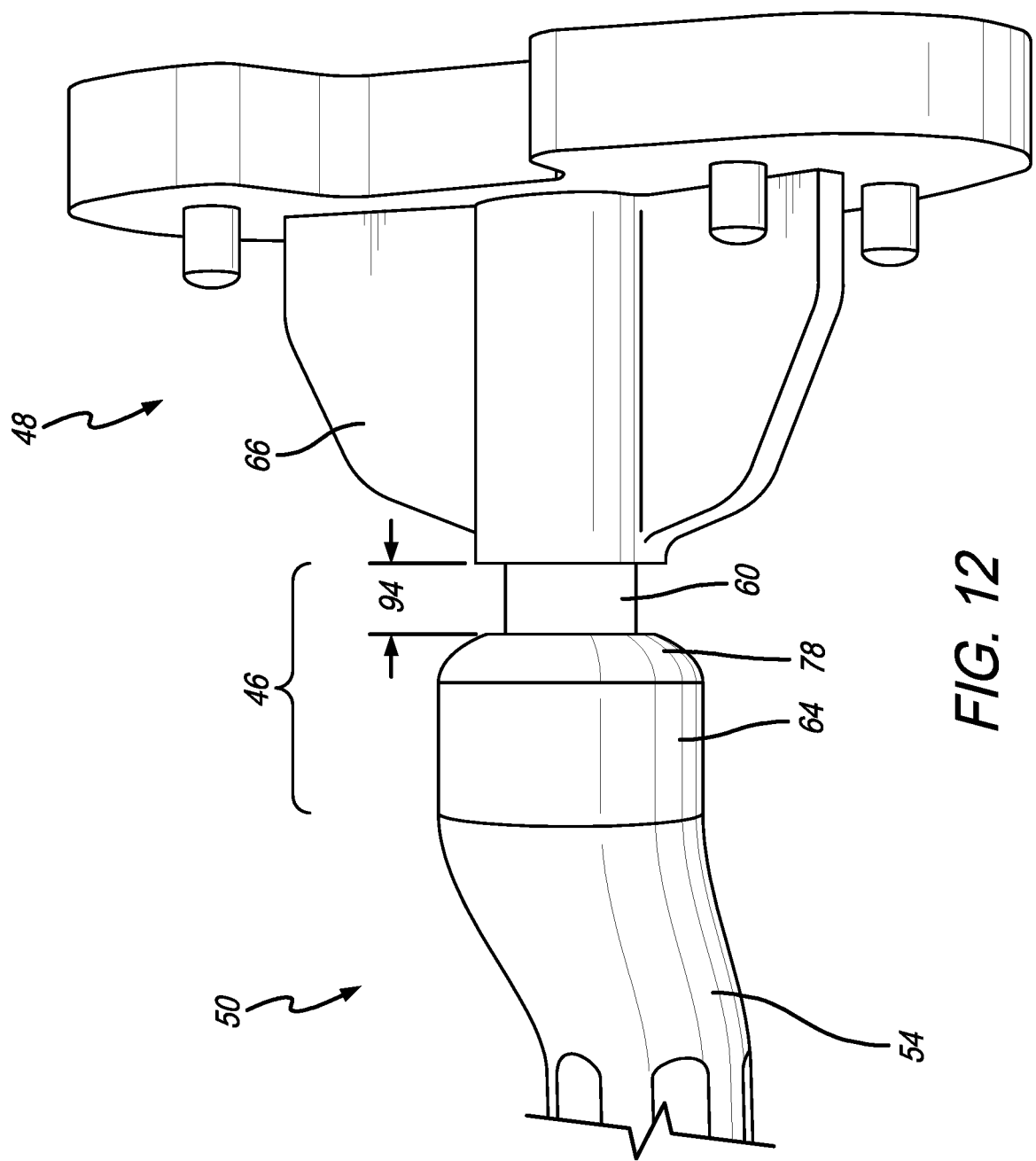
FIG. 12 is an enlarged perspective view similar to FIG. 11, illustrating the eccentric tibial stem threadingly disengaged in linear spaced relation by a desired distance from the tibial baseplate.
Figure 13:
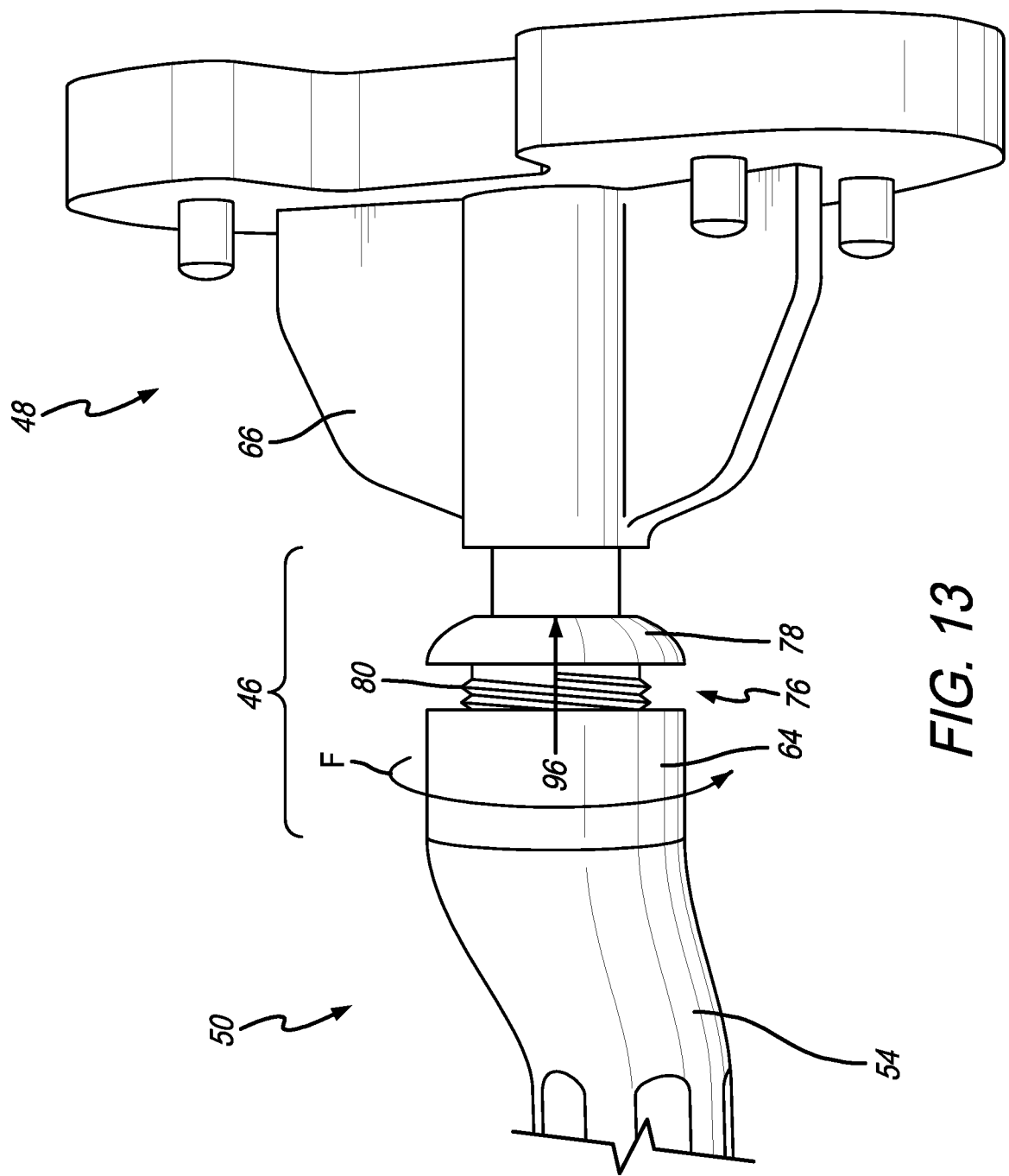
FIG. 13 is an enlarged perspective view similar to FIGS. 11 and 12, illustrating rotation of the lock housing to disengage the extension lock from the lock housing.

To set either the overall length of the tibial implant 48 or to set the eccentricity of the eccentric tibial stem 50, the engagement rod 56 is unscrewed from the tibial baseplate 66, such as by way of conventional disengaging rotation of the threaded section 62. FIG. 12 illustrates one embodiment wherein the eccentric tibial stem 50 has been rotated a desired distance 94 from the tibial baseplate 66.

The next step is to lock the eccentric tibial stem 50 in place in spaced relation relative to the tibial baseplate 66 to maintain its vertical and eccentric positioning relative thereto. In this respect, as shown best in FIG. 13, the lock housing 64 is rotated along rotational arrow F to extend outwardly the locking head 78 of the extension lock 76. In this respect, as described above, the lock housing 64 is vertically restrained in linear spaced relation along the length of the engagement rod 56 by way of the internal lock washer 68, while simultaneously being rotatable relative thereto, and especially with respect to the engagement rod 56. Sufficient clearance between the internal lock washer 68 and the channel 70 may be provided such that the lock housing 64 can engage axially against the upper eccentric section 54 without placing an axial load onto the lock washer 68. Moreover, the extension lock 76 is constrained relative to the eccentric tibial stem 50 by way of locking reception of the inner passage 88 with the planar sides 86 of the rotational lock section 58, otherwise the extension lock 76 would just spin when the lock housing 64 is rotated about its axis. Accordingly, the internal threads 82 of the lock housing 64 selectively engage and/or disengage the external threads 80 of the extension lock 76. When engaged, the external threads 80 thread into the body of the lock housing 64 such that the locking head 78 is in the position generally shown with respect to FIGS. 7-9 and 11. Rotation of the lock housing 64 along the rotational arrow F (FIG. 13) causes commensurate extension of the extension lock 76 out from within the lock housing 64 as generally shown by the directional arrow 96 in FIG. 13. The lock housing 64 is continually rotated until the locking head 78 engages up underneath the tibial baseplate 66 and against the landing surface 92, as best shown in FIG. 14. At this point, the locking head 78 snugly engages the landing surface 92 by friction fit.

But, contrary to the prior art locking system 32 described above, the tibial baseplate 66 may be rotated opposite the lock housing 64 (or conversely, the lock housing 64 may be rotated opposite the tibial baseplate 66) to cause further engagement between the landing surface 92 and the locking head 78. More specifically, rotation of the eccentric tibial stem 50 along rotational arrow G (FIG. 14) causes rotational engagement with the tibial baseplate 66, and vice versa. This would normally decrease the distance 94 but for the obstruction of the now extended locking head 78. The same effect is achieved if the tibial baseplate 66 were rotated relative to the eccentric tibial stem 50 along rotational arrow H, as shown in FIG. 14. In this respect, as also shown in FIG. 14, rotation of the eccentric tibial stem 50 along rotational arrow G causes engagement with the tibial baseplate 66 while continued rotation of the lock housing 64 in the same direction along rotational arrow F causes further extension of the locking head 78 out from within the lock housing 64 and into engagement with the landing surface 92. Advantageously, common rotational movement of the eccentric tibial stem 50 and the lock housing 64, and opposite the tibial baseplate 66, results in enhanced engagement between the locking head 78 and the landing surface 92. This is contrary to the prior art, such as with respect to the prior art locking system 32 described above, wherein common rotation of the angled extension 38 and the locknut 42, such as about the rotational arrows B and C, does not cause common engagement with the tibial baseplate 36 because the locknut 42 is oppositely threaded on the second set of exterior threads 41. Instead, such common rotation, i.e., rotation of the locknut 42 about the rotational arrow C (FIG. 3) causes the locknut 42 to move away (i.e., disengage) the tibial baseplate 36. Thus, not only are the components of the tibial implant 48, including the parts of the locking system 46, all rotated in accordance with convention, dual wrenches or the like are not needed to adequately tighten the locking system 46.

The locking system 46 could be used in knee femur implants, hip femur stem implants, and other joint replacements. The locking system 46 could also be used in the realm of hip, knee, and shoulder arthroplasty, in addition to more esoteric orthopedic implants such as the ankle, elbow, etc.

Although, of course, the locking system 46 disclosed herein could be used with applications outside the use of medical implant devices for positioning one component in linear spaced relation relative to another component. In this respect, the locking system 46 could be used with virtually any mechanical locking device known in the art wherein it is desired to lock two components or devices in linear spaced relation relative to one another about a series of threads. For example, the locking system 46 could replace known methods for using a pair of locknuts which otherwise lock in place along the length of a threaded shaft. On one hand, if the locknuts are commonly threaded, it is easier for the two to dislodge as common rotational movement of one locknut relative to the other will cause easier disengagement, similar to the prior art locking system 32 disclosed above.

Although several embodiments have been described in detail for purposes of illustration, various modifications may be made without departing from the scope and spirit of the invention. Accordingly, the invention is not to be limited, except as by the appended claims.

What is claimed is:

1. An orthopedic implant locking system, comprising:
 an eccentric tibial stem having an engagement rod selectively threadingly engageable with a tibial baseplate;
 a lock housing securable in rotatable and substantial vertical constrained relation relative to the tibial stem via the engagement rod; and
 an extension lock selectively threadingly engageable with the lock housing and including an inner passage keyed to selectively slidably engage the engagement rod in flush engagement therewith, the extension lock extendable relative to the lock housing in response to movement of the lock housing in a first rotational direction simultaneously while the extension lock is in substantial non-rotatable relation relative to the tibial stem and retractable relative to the lock housing in response to movement of the lock housing in a second rotational direction opposite the first rotational direction simultaneously while the extension lock is in substantial non-rotatable relation relative to the tibial stem, wherein engagement of the extension lock with the tibial baseplate generally vertically and rotationally selectively locks the tibial baseplate with the tibial stem.

2. The orthopedic implant locking system of claim 1, wherein the engagement rod includes a keyway configured to selectively receive and retain the inner passage of the extension lock in non-rotatable relation relative thereto and the lock housing includes an inner channel having a size and shape for selectively receiving and retaining a washer freely rotatable therein.

3. The orthopedic implant locking system of claim 2, wherein the keyway comprises at least a pair of planar surfaces cutout from the engagement rod and the washer includes an inner diameter sized for select engagement and retainment within an outwardly presented and generally circumferential collar in the engagement rod for free rotation therein.

4. The orthopedic implant locking system of claim 3, wherein the engagement rod includes a first rotational lock section including the keyway, a threaded section facilitating threaded engagement with the tibial baseplate, and a relatively smooth cylindrical section intermediate the first rotational lock section and the threaded section, and the washer positions the lock housing in a rotatable yet vertically constrained configuration relative to the tibial stem when the washer is simultaneously retained within the inner channel and the collar.

5. The orthopedic implant locking system of claim 2, wherein the washer comprises a general ring shape having a cut-out permitting opposite edges of the general ring-shaped washer to bend relative to one another and the tibial stem includes an adapter having a prefabricated eccentricity.

6. The orthopedic implant locking system of claim 1, wherein the extension lock includes a generally planar locking head that selectively engages a generally planar landing surface of the tibial baseplate for friction fit engagement therewith to lock the tibial baseplate in vertical and non-rotatable relation relative to the tibial stem.

7. The orthopedic implant locking system of claim 6, wherein the first rotational direction comprises a clockwise direction and the second rotational direction comprises a counter-clockwise direction.

8. The locking system of claim 7, wherein rotating the lock housing in the clockwise direction causes the generally planar locking head to engage the generally planar landing surface of the tibial baseplate.

9. The locking system of claim 8, wherein rotating the tibial stem in a clockwise direction causes the generally planar locking head to engage the generally planar landing surface of the tibial baseplate.

10. A locking system, comprising:
 a first component selectively threadingly engageable with a second component;
 a lock housing securable in rotatable and substantial vertical constrained relation relative to the first component; and
 an extension lock selectively threadingly engageable with the lock housing and extendable relative to the lock housing in response to movement of the lock housing in a first rotational direction simultaneously while the extension lock is in substantial non-rotatable relation relative to the first component and retractable relative to the lock housing in response to movement of the lock housing in a second rotational direction opposite the first rotational direction simultaneously while the extension lock is in substantial non-rotatable relation relative to the first component, wherein engagement of the extension lock with the second component generally vertically and rotationally selectively locks the second component with the first component.

11. The locking system of claim 10, wherein the first component includes a keyway configured to selectively receive and retain the extension lock in non-rotatable relation relative thereto.

12. The locking system of claim 11, wherein the keyway comprises at least one pair of planar surfaces cutout from an otherwise generally cylindrical engagement rod extending out from one side of the first component.

13. The locking system of claim 12, wherein the extension lock includes an inner passage keyed to match the at least one pair of planar surfaces for substantial flush engagement therewith when selectively slidably engaged with the engagement rod.

14. The locking system of claim 12, wherein the engagement rod comprises a first rotational lock section including the keyway, a threaded section facilitating threaded engagement with the second component, and a relatively smooth cylindrical section intermediate the first rotational lock section and the threaded section.

15. The locking system of claim 12, wherein the lock housing is in rotatable relation relative to the engagement rod and the extension lock is in non-rotatable relation relative to the engagement rod.

16. The locking system of claim 10, wherein the lock housing includes an inner channel having a size and shape for selectively receiving and retaining a washer freely rotatable therein.

17. The locking system of claim 16, wherein the washer includes an inner diameter sized for select engagement and retainment within an outwardly presented and generally circumferential collar in the first component for free rotation therein.

18. The locking system of claim 17, wherein the washer positions the lock housing in a rotatable yet vertically constrained configuration relative to the first component when the washer is simultaneously retained within the inner channel and the collar.

19. The locking system of claim 16, wherein the washer comprises a general ring shape having a cut-out permitting opposite edges of the general ring-shaped washer to bend relative to one another.

20. The locking system of claim 10, wherein the first component includes a first lower elongated section and a second upper eccentric section generally axially misaligned from the first lower elongated section.

21. The locking system of claim 20, wherein the first component comprises an eccentric tibial stem and the second component comprises a tibial baseplate.

22. The locking system of claim 10, wherein the first component comprises an adapter having a prefabricated eccentricity.

23. The locking system of claim 10, wherein the extension lock includes a generally planar locking head that selectively engages a generally planar landing surface of the second component for friction fit engagement therewith to lock the second component in vertical and non-rotatable relation relative to the first component.

24. The locking system of claim 23, wherein the first rotational direction comprises a clockwise direction and the second rotational direction comprises a counter-clockwise direction, and wherein rotation of the second component relative to the lock housing causes engagement between the locking head and the landing surface.

25. The locking system of claim 24, wherein rotating the first component and the lock housing relative to the second component in a common rotational direction causes engagement between the locking head and the landing surface.

26. A locking system, comprising:
a first component selectively threadingly engageable with a second component;
a lock housing including an inner channel having a size and shape for selectively receiving and retaining a washer freely rotatable therein and securable in rotatable and substantial vertical constrained relation to the first component; and
an extension lock selectively threadingly engageable with the lock housing and selectively slidably engageable with the first component having a keyway configured to retain the extension lock in non-rotatable relation relative to the first component, the extension lock extendable relative to the lock housing in response to movement of the lock housing in a first rotational direction simultaneously while the extension lock is in substantial non-rotatable relation relative to the first component and retractable relative to the lock housing in response to movement of the lock housing in a second rotational direction opposite the first rotational direction simultaneously while the extension lock is in substantial non-rotatable relation relative to the first component;
wherein engagement of a generally planar locking head of the extension lock with a generally planar landing surface of the second component generally vertically and rotationally selectively locks the second component with the first component; and
wherein the first rotational direction comprises a clockwise direction and the second rotational direction comprises a counter-clockwise direction.

27. The locking system of claim 26, wherein the keyway comprises at least one pair of planar surfaces cutout from an otherwise generally cylindrical engagement rod extending out from one side of the first component and the extension lock includes an inner passage keyed to match the at least one pair of planar surfaces for substantial flush engagement therewith when selectively slidably engaged with the engagement rod.

28. The locking system of claim 27, wherein the lock housing is in rotatable relation relative to the engagement rod and the extension lock is in non-rotatable relation relative to the engagement rod, the engagement rod comprising a first rotational lock section including the keyway, a threaded section facilitating threaded engagement with the second component, and a relatively smooth cylindrical section intermediate the first rotational lock section and the threaded section.

29. The locking system of claim 26, wherein the washer comprises a general ring shape having a cut-out permitting opposite edges thereof to bend relative to one another and includes an inner diameter sized for select engagement and retainment within an outwardly presented and generally circumferential collar in the first component for free rotation therein, the washer positioning the lock housing in a rotatable yet vertically constrained configuration relative to the first component when the washer is simultaneously retained within the inner channel and the collar.

30. The locking system of claim 26, wherein the first component comprises an eccentric tibial stem including a first lower elongated section and a second upper eccentric section generally axially misaligned from the first lower elongated section and the second component comprises a tibial baseplate.

31. The locking system of claim 26, wherein the first component comprises an adapter having a prefabricated eccentricity.

\* \* \* \* \*